US010185803B2

(12) United States Patent
Frey et al.

(10) Patent No.: US 10,185,803 B2
(45) Date of Patent: Jan. 22, 2019

(54) SYSTEMS AND METHODS FOR CLASSIFYING, PRIORITIZING AND INTERPRETING GENETIC VARIANTS AND THERAPIES USING A DEEP NEURAL NETWORK

(71) Applicant: DEEP GENOMICS INCORPORATED, Toronto (CA)

(72) Inventors: Brendan Frey, Toronto (CA); Michael K. K. Leung, Toronto (CA); Andrew Thomas Delong, Toronto (CA); Hui Yuan Xiong, Toronto (CA); Babak Alipanahi, Toronto (CA); Leo J. Lee, Toronto (CA); Hannes Bretschneider, Toronto (CA)

(73) Assignee: DEEP GENOMICS INCORPORATED, Toronto (CA)

( * ) Notice: Subject to any disclaimer, the term of this patent is extended or adjusted under 35 U.S.C. 154(b) by 224 days.

(21) Appl. No.: 14/739,432

(22) Filed: Jun. 15, 2015

(65) Prior Publication Data

US 2016/0364522 A1 Dec. 15, 2016

(51) Int. Cl.
*G06F 19/00* (2018.01)
*G06F 19/22* (2011.01)
(Continued)

(52) U.S. Cl.
CPC .............. *G06F 19/22* (2013.01); *G06F 19/24* (2013.01); *G06N 3/04* (2013.01); *G06F 19/18* (2013.01)

(58) Field of Classification Search
CPC .......... G06F 19/20; G06F 19/18; G06F 19/22; G06F 19/24; G06F 19/28; G06F 19/00;
(Continued)

(56) References Cited

U.S. PATENT DOCUMENTS 6,128,609 A 10/2000 Rose
8,697,359 B1 4/2014 Zhang
(Continued)

FOREIGN PATENT DOCUMENTS

WO WO-9412948 A1 6/1994
WO 2013070634 5/2013
(Continued)

OTHER PUBLICATIONS

Hinton, et al. Distilling the knowledge in a neural network. arXiv preprint arXiv:1503.02531 (2015).
(Continued)

*Primary Examiner* — Mary K Zeman
(74) *Attorney, Agent, or Firm* — Wilson Sonsini Goodrich & Rosati

(57) ABSTRACT

Described herein are systems and methods that receive as input a DNA or RNA sequence, extract features, and apply layers of processing units to compute one ore more condition-specific cell variables, corresponding to cellular quantities measured under different conditions. The system may be applied to a sequence containing a genetic variant, and also to a corresponding reference sequence to determine how much the condition-specific cell variables change because of the variant. The change in the condition-specific cell variables are used to compute a score for how deleterious a variant is, to classify a variant's level of deleteriousness, to prioritize variants for subsequent processing, and to compare a test variant to variants of known deleteriousness. By modifying the variant or the extracted features so as to incorporate the effects of DNA editing, oligonucleotide therapy, DNA- or RNA-binding protein therapy or other therapies, the system may be used to determine if the deleterious effects of the original variant can be reduced.

22 Claims, 19 Drawing Sheets

(51) Int. Cl.
*G06F 19/24* (2011.01)
*G06N 3/04* (2006.01)
*G06F 19/18* (2011.01)

(58) Field of Classification Search
CPC .......... G06F 19/12; G06F 19/16; G06F 19/26; G06F 19/14; G06F 19/30; G06F 19/701; G06F 17/13; G06F 17/14; G06F 19/10; C12Q 2600/156; C12Q 1/6883; C12Q 2537/165; C12Q 2600/118; C12Q 1/6827; C12Q 2600/112; C12Q 2600/172; C12Q 1/68; G16H 50/20; G01N 2800/50; G01N 2800/56; G06N 3/04; G06N 3/08; G06N 3/084; G06N 99/005
See application file for complete search history.

(56) References Cited

U.S. PATENT DOCUMENTS

| | | | |
|---|---|---|---|
| 9,406,017 | B2 | 8/2016 | Hinton et al. |
| 2008/0300797 | A1 | 12/2008 | Tabibiazar et al. |
| 2012/0310539 | A1 | 12/2012 | Crockett et al. |
| 2013/0096838 | A1 | 4/2013 | Fairbrother |
| 2013/0332081 | A1 | 12/2013 | Reese et al. |
| 2014/0011977 | A1 | 1/2014 | Krainer et al. |
| 2014/0199698 | A1 | 7/2014 | Rogan et al. |
| 2014/0280327 | A1 | 9/2014 | Pham et al. |
| 2014/0359422 | A1 | 12/2014 | Bassett, Jr. et al. |
| 2015/0066378 | A1 | 3/2015 | Robison et al. |
| 2015/0100530 | A1 | 4/2015 | Mnih et al. |
| 2017/0024642 | A1 | 1/2017 | Xiong et al. |
| 2018/0165412 | A1 | 6/2018 | Frey et al. |

FOREIGN PATENT DOCUMENTS

| | | |
|---|---|---|
| WO | WO-2016145516 A1 | 9/2016 |
| WO | WO-2016201564 A1 | 12/2016 |
| WO | WO-2017190211 A1 | 11/2017 |
| WO | WO-2017193198 A | 11/2017 |

OTHER PUBLICATIONS

Hinton, et al. Improving neural networks by preventing co-adaptation of feature detectors. arXiv preprint arXiv:1207.0580 (2012).

International Search Report for PCT/CA2016/050273, dated Jun. 15, 2016.

Srivastava, et al. Dropout: a simple way to prevent neural networks from overfilling. Journal of Machine _earning Research 15.1 (2014): 1929-1958.

Written Opinion of the International Search Authority for PCT/CA2016/050273, dated Jun. 15, 2016.

Leung, M. K. K., Xiong, H. Y., Lee, L. J., Frey, B. J. Deep learning of the tissue-regulated splicing code. Bioinformatics vol. 30, pp. i121-i129, Jun. 15, 2014.

Xiong, H. Y., Alipanahi, B., Lee, L. J., Bretschneider, H., Merico, D., Yuen, R. K. C., Hua, Y., Gueroussov, S., Najafabadi, H. S., Hughes, T. R., Morris, Q., Barash, Y. Krainer, A. R., Jojic, N. Scherer, S. W., Blencowe, B. J., Frey, B. J. The human splicing code reveals new insights into the genetic determinants of disease. Science DOI: 10.1126/science.1254806. Published Online Dec. 18, 2014.

Barash, Y., Calarco, J. A., Gao, W., Pan, Q., Wang, X., Shai, O., Blencowe, B. J., Frey, B. J. Deciphering the splicing code. Nature. May 6, 2010;465 (7294):53-9. doi: 10.1038/nature09000.

Quang, D., Chen, Y., Xie X. Dann: A deep learning approach for annotating the pathogenicity of genetic variants. Bioinformatics. Mar. 1, 2015;31(5):761-3. doi: 10.1093/bioinformatics/btu703. Epub Oct. 22, 2014.

Reese, M. G. Application of a time-delay neural network to promoter annotation in the *Drosophila melanogaster* genome. Comput Chem. Dec. 2001;26(1):51-6.

Hebsgaard, S. M., Korning, P. G., Tolstrup, N., Engelbrecht, J., Rouzé, P., Brunak, S. Splice site prediction in *Arabidopsis thaliana* pre-mRNA by combining local and global sequence information. Nucleic Acids Res. Sep. 1, 1996;24(17):3439-52.

Hatzigeorgiou, A., Mache, N., Reczko, M. Functional site prediction on the DNA sequence by artificial neural networks. IEEE International Joint Symposia on Intelligence and Systems, Nov. 4-5, 1996, p. 12-17, Print ISBN: 0-8186-7728-7.

International Search Report corresponding to PCT/CA2016/050689; Canadian Intellectual Property Office; dated Jun. 27, 2016.

Written Opinion of the International Searching Authority corresponding to PCT/CA2016/050689; Canadian Intellectual Property Office; dated Jul. 27, 2016.

International search report dated Mar. 6, 2017 for PCT Application No. PCT/CA2016/050776.

International search report dated Dec. 22, 2016 for PCT Application No. PCT/CA2016/050510.

1400

1402

SYSTEMS AND METHODS FOR CLASSIFYING, PRIORITIZING AND INTERPRETING GENETIC VARIANTS AND THERAPIES USING A DEEP NEURAL NETWORK

TECHNICAL FIELD

The following relates generally to systems and methods for classifying, prioritizing and interpreting genetic variants and therapies using a deep neural network.

BACKGROUND

Precision medicine, genetic testing, therapeutic development and whole genome, exome, gene panel and mini-gene reporter analysis require the ability to accurately interpret how diverse features encoded in the genome, such as protein binding sites, RNA secondary structures, and nucleosome positions, impact processes within cells. Most existing approaches to identifying disease variants ignore their impact on these genomic features. Many genome studies are restricted to mutations in exons that either change an amino acid in a protein or prevent the production of the protein.

Over the past decade, the importance of understanding regulatory genomic instructions and not just the protein-coding exons and genes that they control has been underscored by several observations: While evolution is estimated to preserve at least 5.5% of the human genome, only 1% accounts for exons within genes; biological complexity often cannot be accounted for by the number of genes (e.g. balsam poplar trees have twice as many genes as humans); differences between organisms cannot be accounted for by differences between their genes (e.g. less than 1% of human genes are distinct from those of mice and dogs); increasingly, disease-causing variants have been found outside of exons, indicating that crucial information is encoded outside of those sequences.

In traditional molecular diagnostics, an example workflow may be as follows: a blood or tissue sample is obtained from a patient; variants (mutations) are identified, by either sequencing the genome, the exome or a gene panel; the variants are individually examined manually (e.g. by a technician), using literature databases and internet search engines; a diagnostic report is prepared. Manually examining the variants is costly and prone to human error, which may lead to incorrect diagnosis and potential patient morbidity. Automating or semi-automating this step is thus beneficial. Since the number of possible genetic variants is large, evaluating them manually is time-consuming, highly dependent on previous literature, and involves experimental data that has poor coverage and therefore can lead to high false negative rates, or "variants of unknown significance". The same issues arise in therapeutic design, where the number of possible therapies (molecules) to be evaluated is extremely large.

Techniques have been proposed for which predicting phenotypes (e.g., traits and disease risks) from the genome can be characterized as a problem suitable for solution by machine learning, and more specifically by supervised machine learning where inputs are features extracted from a DNA sequence (genotype), and the outputs are the phenotypes. Such an approach is shown in FIG. 2(a). A DNA sequence 204 is fed to a predictor 202 to generate outputs 208, such as disease risks. This approach is unsatisfactory for most complex phenotypes and diseases for two reasons. First is the sheer complexity of the relationship between genotype (represented by 204) and phenotype (represented by 208). Even within a single cell, the genome directs the state of the cell through many layers of intricate biophysical processes and control mechanisms that have been shaped by evolution. It is extremely challenging to infer these regulatory processes by observing only the genome and phenotypes, for example due to 'butterfly effects'. For many diseases, the amount of data necessary would be cost-prohibitive to acquire with currently available technologies, due to the size of the genome and the exponential number of possible ways a disease can be traced to it. Second, even if one could infer such models (those that are predictive of disease risks), it is likely that the hidden variables of these models would not correspond to biological mechanisms that can be acted upon, unless strong priors, such as cause-effect relationships, have been built in. This is important for the purpose of developing therapies. Insisting on how a model ought to work by using these priors can hurt model performance if the priors are inaccurate, which they usually are.

Some other machine learning approaches to genetic analysis have been proposed. One such approach predicts a cell variable that combines information across conditions, or tissues. Another describes a shallow, single-layer Bayesian neural network (BNN), which often relies on methods like Markov Chain Monte Carlo (MCMC) to sample models from a posterior distribution, which can be difficult to speed up and scale up to a large number of hidden variables and a large volume of training data. Furthermore, computation-wise, it is relatively expensive to get predictions from a BNN, which require computing the average predictions of many models.

SUMMARY

In one aspect, a method for computing variant-induced changes in one or more condition-specific cell variables for one or more variants is provided, the method comprising: computing a set of variant features from a DNA or RNA variant sequence; applying a deep neural network of at least two layers of processing units to the variant features to compute one or more condition-specific variant cell variables; computing a set of reference features from a DNA or RNA reference sequence; applying the deep neural network to the reference features to compute one or more condition-specific reference cell variables; computing a set of variant-induced changes in the one or more condition-specific cell variables by comparing the one or more condition-specific reference cell variables to the one or more condition-specific variant cell variables.

In another aspect, a deep neural network for computing variant-induced changes in one or more condition-specific cell variables for one or more variants is provided, the deep neural network comprising: an input layer configured to receive as input a set of variant features from a DNA or RNA variant sequence; and at least two layers of processing units operable to: compute one or more condition-specific variant cell variables; compute a set of reference features from a DNA or RNA reference sequence; compute one or more condition-specific reference cell variables; compute a set of variant-induced changes in the one or more condition-specific cell variables by comparing the one or more condition-specific reference cell variables to the one or more condition-specific variant cell variables.

In another aspect, a method for training a deep neural network to compute one or more condition-specific cell variables is provided, the method comprising: establishing a neural network comprising at least two connected layers of processing units; repeatedly updating one or more parameters of the neural network so as to decrease the error for a set of training cases chosen randomly or using a predefined pattern, where each training case comprises features extracted from a DNA or RNA sequence and corresponding targets derived from measurements of one or more condition-specific cell variables, until a condition for convergence is met at which point the parameters are no longer updated.

DESCRIPTION OF THE DRAWINGS

The features of the invention will become more apparent in the following detailed description in which reference is made to the appended drawings wherein.

DETAILED DESCRIPTION

Figure 1:
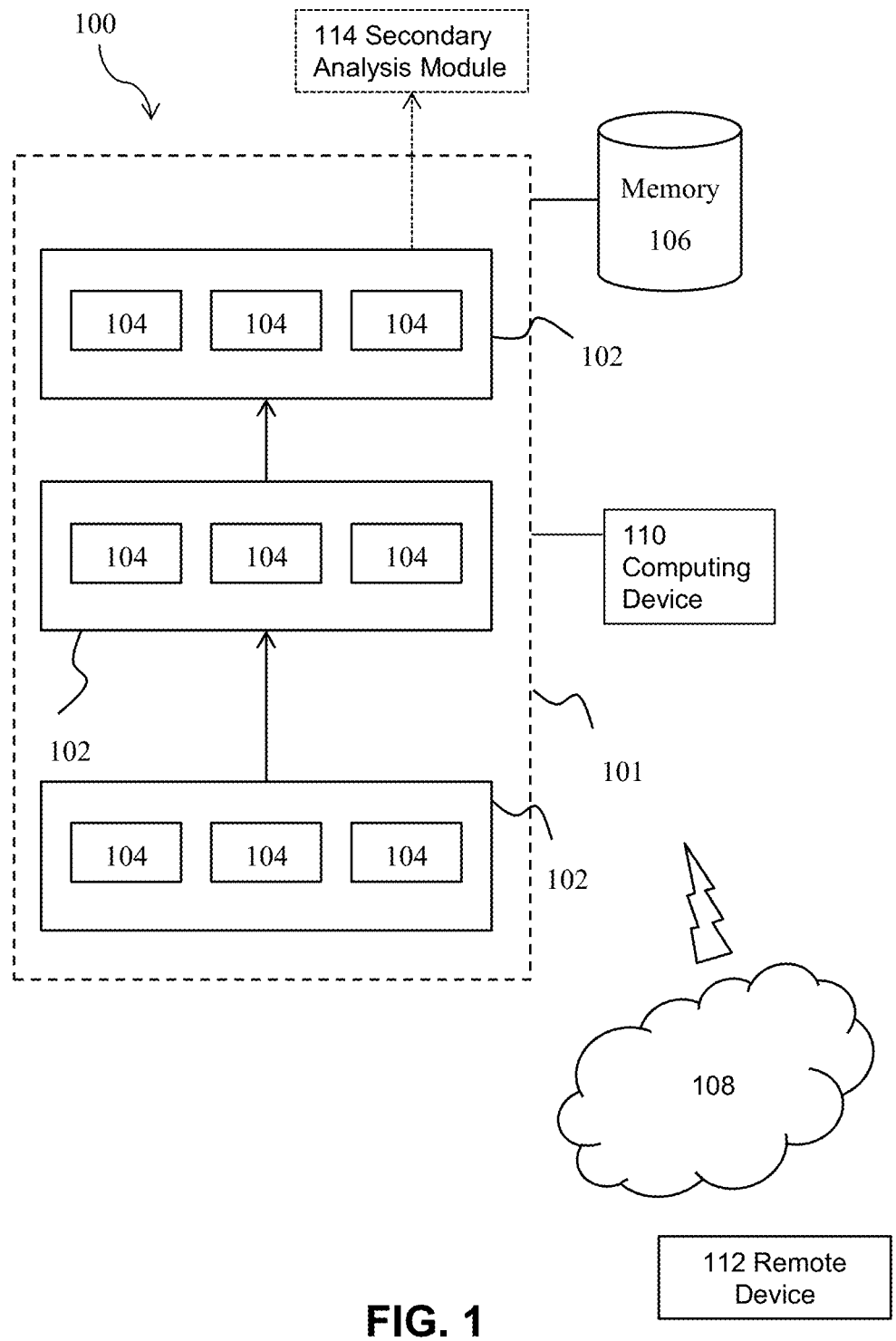
FIG. 1 is an system for cell variable prediction.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Systems and methods described herein relate, in part, to the problem of assessing genetic variants with respect to phenotypes, such as deleteriousness for human diseases. This problem has implications in several industrial categories under the broad umbrella of 'personalized medicine', including molecular diagnostics, whole genome sequencing, and pharmaceutical development.

It has been found that the effect of a variant depends on genetic context, which includes which other variants are present and, more generally, on the genomic sequence within the individual, or patient, being tested. So, whereas a particular variant may be benign in one genetic context, it may cause a disease in another genetic context. This impacts prioritization and interpretation. The following describes a process for context-dependent genetic variant assessment and wherein variants may be ranked and presented as a priority list. Variant prioritization can be used to increase efficiency and accuracy of manual interpretation, since it enables the technician to focus on a small subset of candidates Computational procedures for prioritizing and/or interpreting variants must generalize well. Generalization refers to the ability of the computational procedure to assess variants that have not been seen before and that may be involved in a disease that has not been previously analyzed. A method that generalizes well should even be able to assess variants within genes that have not been previously analyzed for variants. Finally, a crucial aspect of enabling computational procedures to operate effectively is computational efficiency since these procedures may involve aggregating, organizing and sifting through large amounts of data.

The systems and methods described herein apply deep learning to genetic variant analysis. Deep learning generally refers to methods that map data through multiple levels of abstraction, where higher levels represent more abstract entities. The goal of deep learning is to provide a fully automatic system for learning complex functions that map inputs to outputs, without using hand crafted features or rules. One implementation of deep learning comes in the form of feedforward neural networks, where levels of abstraction are modeled by multiple non-linear hidden layers.

In brief, embodiments described herein provide systems and methods that receive as input a DNA or RNA sequence, extracts features, and apply multiple layers of nonlinear processing units of a cell variable predictor ("CVP") to compute a cell variable, which corresponds to a measurable quantity within a cell, for different conditions, such as tissue types. To distinguish a cell variable that corresponds to a measureable quantity for a specific condition, such as a tissue type, from a cell variable that is a combination of measureable quantities from multiple conditions, we refer to the former as a "condition-specific cell variable" and the latter as a "non-specific cell variable". In embodiments, the CVP is applied to a DNA or RNA sequence and/or features extracted from the sequences, containing a genetic variant, and also to a corresponding reference (e.g., wild type) sequence to determine how much the cell variable changes because of the variant. The systems and methods can be applied to naturally occurring genomic sequences, minigene reporters, edited genomic sequences, such as those edited using CRISPR-Cas9, genomic sequences targeted by therapies, and other genomic sequences. The change in the cell variable in different conditions may be used to classify disease-causing variants, compute a score for how deleterious a variant is, prioritize variants for subsequent processing, interpret the mechanism by which a variant operates, and determine the effect of a therapy. Further, an unknown variant can be given a high score for deleteriousness if it induces a change in a particular cell variable that is similar to changes in the same cell variable that are induced by one or more variants that are known to be deleterious.

In embodiments, the CVP comprises a deep neural network having multiple layers of processing units and possibly millions of parameters. The CVP may be trained using a dataset of DNA or RNA sequences and corresponding measurements of cell variables, using a deep learning training method that adjusts the strengths of the connections between processing units in adjacent layers. Specialized training methods are described, including a multi-task training method that improves accuracy. The mechanism by which a mutation causes a deleterious change in a cell variable may in some instances be determined by identifying features or groups of features that are changed by the mutation and that cause the cell variable to change, which can be computed by substituting features derived from the variant sequence one by one into the reference sequence or by backpropagating the cell variable change back to the input features.

If a change related to a variant of any cell variable is large enough compared to a reference, the variant warrants investigation for deleteriousness. The systems described herein can thus be used to prioritize genetic variants for further 'wet-lab' investigations, significantly aiding and reducing the costs of variant discovery. Furthermore, because of the presence of cell variables in the predictor, the invention can assign 'blame' to variants that are disease causing, and generate appropriate user visualizations. For example, a variant that changes the splicing 'cell variable' may be targeted by a therapy that targets the splicing pathway to remediate the disease As used herein, the term "reference sequence" means: in the context of evaluating a variant (as described below), whereupon the systems described herein compare the variant to a 'reference sequence', the reference sequence is a DNA or RNA sequence obtained using genome sequencing, exome sequencing or gene sequencing of an unrelated individual or a closely related individual (e.g., parent, sibling, child). Alternatively, the reference sequence may be derived from the reference human genome, or it may be an artificially designed sequence.

As used herein, the term "variant" means: a DNA or RNA sequence that differs from a reference sequence in one or more nucleotides, by substitutions, insertions, deletions or any other changes. The variant sequence may be obtained using genome sequencing, exome sequencing or gene sequencing of an individual. Alternatively, the variant sequence may be derived from the reference human genome, or it may be an artificially designed sequence. For the purpose of this invention, when a variant is being evaluated by the system, the sequence containing the variant as well as surrounding DNA or RNA sequence is included in the 'variant'.

As used herein, the term "single nucleotide variant" ("SNV") means: a variant that consists of a substitution to a single nucleotide.

As used herein, the term "variant analysis" means: the procedure (computational or otherwise) of processing a variant, possibly in addition to surrounding DNA or RNA sequence that establishes context, for the purpose of variant scoring, categorization, prioritization, and interpretation.

As used herein, the term "score" means: a numeric value that indicates how deleterious a variant is expected to be.

As used herein, the term "classification" refers to the classification of a variant. A variant may be classified in different ways, such as by applying a threshold to the score to determine if the variant is deleterious or not. The American College of Medical Genetics recommends a five-way classification: pathogenic (very likely to contribute to the development of disease); likely pathogenic (there is strong evidence that the variant is pathogenic, but the evidence is inconclusive); unknown significance or VUS (there is not enough evidence to support classification one way or another); likely benign (there is strong evidence that the variant is benign, but the evidence is inconclusive); benign (very likely to be benign).

As used herein, the terms "rank"/"prioritization" mean: the process of sorting the scores of a set of variants to determine which variant should be further investigated. The pathogenic variants will be at the top, with the benign variants at the bottom.

As used herein, the term "cell variable" means: a quantity, level, potential, or process outcome in the cell that is potentially relevant to the function of a living cell, and that is computed by a CVP (see below). There are two types of cell variables: a "condition-specific cell variable" is a cell variable that is measured or predicted under a specific condition, such as a tissue type; a "non-specific cell variable" is a cell variable that is derived by combining information from across multiple conditions, for example by subtracting the average cell variable values across conditions from the cell variable for each condition. A cell variable can often be quantified by a vector of one or more real-valued numbers, or by a probability distribution over such a vector. Examples include the strength of binding between two molecules (e.g. protein-protein or protein-DNA binding), exon splicing levels (the fraction of mRNA transcripts in a particular tissue that contain a particular exon, i.e. percent spliced in), DNA curvature, DNA methylation, RNA folding interactions.

As used herein, the term "event" means: in the context of a splicing-related cell variable (e.g. the fraction of transcripts with an exon spliced in), an observed (measured) alternative splicing event in the cell where both the genomic features and the corresponding splicing levels are known for that particular event. Each event can be used as either a training case or a testing case for a machine learning system.

Referring now to FIG. 1, shown therein is a system 100 for cell variable prediction, comprising a machine learning unit. The machine learning unit is preferably implemented by a deep neural network, which is alternatively referred to herein as a "cell variable predictor" ("CVP") 101. The CVP takes as input a set of features, including genomic features, and produces an output intended to mimic a specific cell variable. The quantification of a cell variable can be represented in such a system by one or more real-valued numbers on an absolute or relative scale, with or without meaningful units. In embodiments, the CVP may provide other outputs in addition to outputs intended to mimic a specific cell variable.

The system 100 further comprises a memory 106 communicatively linked to the CVP 101.

An illustrated embodiment of the CVP 101 comprising a feedforward neural network having a plurality of layers 102 (i.e. deep) is shown. Each layer comprises one or more processing units 104, each of which implements a feature detector and/or a computation that maps an input to an output. The processing units 104 accept a plurality of parameter inputs from other layers and apply activation functions with associated weights for each such parameter input to the respective processing unit 104. Generally, the output of a processing unit of layer 1 may be provided as input to one or more processing units of layer l+1.

Each processing unit may be considered as a processing "node" of the network and one or more nodes may be implemented by processing hardware, such as a single or multi-core processor and/or graphics processing unit(s) (GPU(s)). Further, it will be understood that each processing unit may be considered to be associated with a hidden unit or an input unit of the neural network for a hidden layer or an input layer, respectively. The use of large (many hidden variables) and deep (multiple hidden layers) neural networks may improve the predictive performances of the CVP compared to other systems.

In embodiments, inputs to the input layer of the CVP can include genetic information, such as sequences representing DNA, RNA, features derived from DNA and RNA, and features providing extra information (e.g. tissue type, age, sex), while outputs at the output layer of the CVP can include cell variables.

It will be appreciated that though an illustrative feedforward network is described herein, the type of neural network implemented is not limited merely to feedforward neural networks but can also be applied to any neural networks, including convolutional neural networks, recurrent neural networks, auto-encoders and Boltzmann machines.

In embodiments the system 100 comprises a secondary analysis unit 114 for receiving the cell variables from the output layer and providing further analysis, as described below.

The memory 106 may comprise a database for storing activations and learned weights for each feature detector, as well as for storing datasets of genetic information and extra information and optionally for storing outputs from the CVP 101. The genetic information may provide a training set comprising training data. The training data may, for example, be used for training the CVP 101 to predict cell variables, in which case DNA and RNA sequences with known cell variables and/or phenotypes may be provided. The memory 106 may further store a validation set comprising validation data.

Generally, during the training stage, the neural network learns optimized weights for each processing unit. After learning, the optimized weight configuration can then be applied to test data. Stochastic gradient descent can be used to train feedforward neural networks. A learning process (backpropagation), involves for the most part matrix multiplications, which makes them suitable for speed up using GPUs. Furthermore, the dropout technique may be utilized to prevent overfitting.

The system may further comprise a computing device 110 communicatively linked to the CVP 101 for controlling operations carried out in the CVP. The computing device may comprise further input and output devices, such as input peripherals (such as a computer mouse or keyboard), and/or a display. The computing device 110 may further be linked to a remote device 112 over a wired or wireless network 108 for transmitting and receiving data. In embodiments, genetic information is received over the network 108 from the remote device 112 for storage in memory 106. Cell variable predictions and lists of variants priorities may be displayed to a user via the display.

Figure 2:
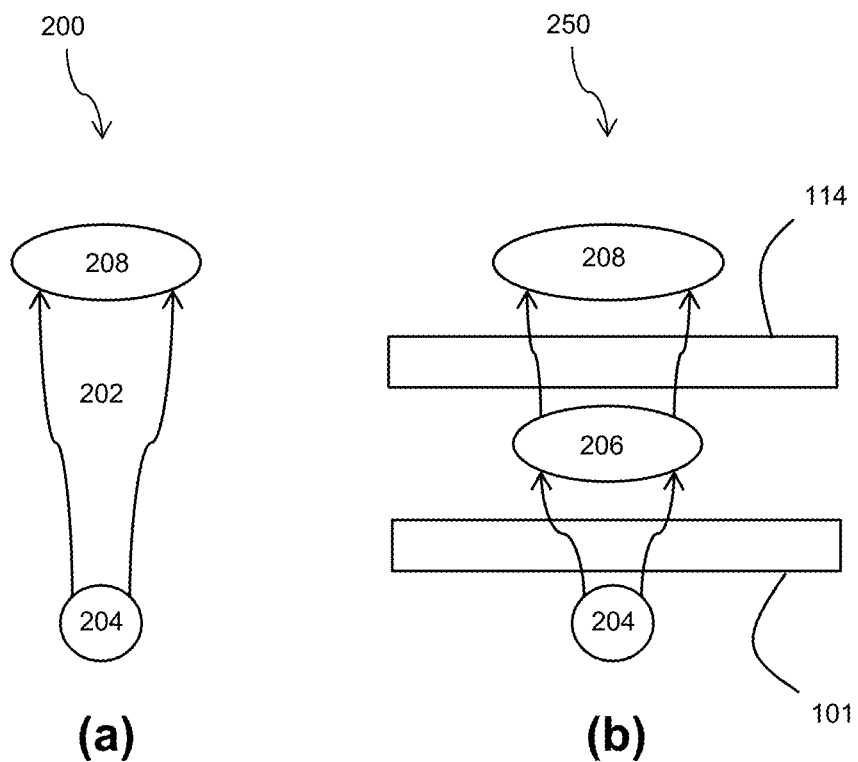
FIG. 2 shows a comparison of approaches to predict phenotypes, such as disease risks, from an input.

Referring now to FIG. 2, shown therein is a comparison of a prior (FIG. 2(a)) and currently described (FIG. 2(b)) machine learning process to predict phenotypes, such as disease risks or deleteriousness from a genotype. Contrary to the prior approach, which was described above, the currently described process predicts a cell variable as an intermediate to the phenotype. As described above, the inputs 204 to a CVP can include sequences representing DNA, RNA, features derived from DNA and RNA, and features providing extra information (e.g. tissue type, age, sex). The cell variables 206 could be, for example, the distribution of proteins along a strand of DNA containing a gene, the number of copies of a gene (transcripts) in a cell, the distribution of proteins along the transcript, and the number of proteins. Once determined, the cell variables can be used by the system to determine how much a variant causes the cell variable to change. By examining how much a mutation causes the cell variable to change, the CVP can be used to score, categorize, and prioritize variants. Specifically, once determined, the cell variable predictions can act as high-level features to facilitate more accurate phenotypic predictions, optionally performed at the secondary analysis unit 114. By training predictors that predict how genotype influences cell variables, such as concentrations of proteins, the resultant machine learning problem is modularized. Moreover, it allows variants to be related to particular cell variables, thereby providing a mechanism to explain variants.

In one embodiment, the variant and a reference sequence are fed into the input layer of the CVP 101 and the amount of change in the cell variable is quantified and used to score, categorize and prioritize the variant by the secondary analysis unit 114.

In another embodiment, the secondary analysis unit 114 comprises a second system (of similar architecture to the CVP) trained to predict a phenotype based on the outputs of the cell variable prediction systems (as illustrated in FIG. 2b). For example, in the case of spinal muscular atrophy, the cell variable could be the frequency with which the exon is included when the gene is being copied to make a protein. Other examples of cell variables include the distribution of proteins along a strand of DNA containing a gene, the number of copies of a gene (transcripts) in a cell, the distribution of proteins along the transcript, and the number of proteins.

The CVP comprises multiple layers of nonlinear processing units to compute the cell variable using the raw DNA or RNA sequence, or features derived from the sequence. In embodiments, in order to quantify the effect of a variant, the system may first construct a pair of feature vectors corresponding to the reference sequence and the variant sequence. Due to the variant, these genomic feature vectors will be different, but without a further cell variable predictor it may not be possible to predict whether those differences would result in any change in phenotype. Embodiments of the predictive system may therefore infer both the reference cell variable value and the variant cell variable value using these two distinct feature vectors. After that, a distance function that combines the reference and the variant predictions may be used to produce a single score which summarizes the magnitude of predicted effect induced by the mutations. Example distance functions include the absolute difference in expectation, Kullback-Leibler divergence, and variation distance. Detailed mathematical formulas of these will be described in a later paragraph.

It will be appreciated that process 250 can rely on input features derived from other types of data besides DNA sequences (e.g. age, sex, known biomarkers)—the above described inputs are merely illustrative.

An aspect of the embodiments described herein is the use of machine learning to infer predictors that are capable of generalizing to new genetic contexts and to new cell states. For example, a predictor may be inferred using reference genome and data profiling transcripts in healthy tissues, but then applied to the genome of a cancer cell to ascertain how the distribution of transcripts changes in the cancer cell. This notion of generalization is a crucial aspect of the predictors that need to be inferred. If a predictor is good at generalization, it can analyze variant sequences that lead to changes in cell variables that may be indicative of disease state, without needing experimental measurements from diseased cells.

Process 250 may address the two problems discussed with respect to approach 200. Since the cell variables are more closely related to and more easily determined from genomic sequences than are phenotypes, learning predictors that map from DNA to cell variables is usually more straightforward. High-throughput sequencing technologies are currently generating massive amounts of data profiling these cell variables under diverse conditions; these datasets can be used to train larger and more accurate predictors. Also, since the cell variables correspond to intermediate biochemically active quantities, such as the concentration of a gene transcript, they may be good targets for therapies. If high disease risk is associated with a change in a cell variable compared to a healthy individual, an effective therapy may consist of restoring that cell variable to its normal state. Embodiments may include such cell variables as 'exon inclusion or exclusion', 'alternative splice site selection', 'alternative polyadenylation site selection', 'RNA- or DNA-binding protein or microRNA specificity', and 'phosphorylation'.

Various aspects of the current system and method include: the method can be applied to raw DNA or RNA sequence or features extracted from the sequence, such as RNA secondary structures and nucleosome positions; the method can compute one or more condition-specific cell variables, without the need for a baseline average across conditions; the method can detect variants that affect all condition-specific cell variables in the same way; the method can compare a variant sequence to a reference sequence, enabling it to make different predictions for the same variant, depending on genetic context; the method can compute the condition-specific cell variables using a deep neural network, which has at least two layers of processing units; the method does not require disease labels (e.g., a case population and a control population); the method can score a variant that has never been seen before; the method can be used to compute a 'distance' between a variant sequence and a reference sequence, which can be used to rank the variant; the method can be used to compute a 'distance' between variants, which is useful for classifying unknown variants based on how similar they are to known variants.

In the following sections, systems and methods for creating a condition-specific cell variable predictor for cassette splicing are described in further detail. First, production of training targets, and generation of outputs using the systems and methods will be described. Subsequently, the procedure for training and optimizing a deep neural network (DNN), such as the CVPs, on a sparse and unbalanced biological dataset will be described. Subsequently, example methods to analyze the outputs of the systems will be described. Further, techniques to analyze the behaviour of such a DNN in terms of its inputs and gradients will be described.

Figure 3:
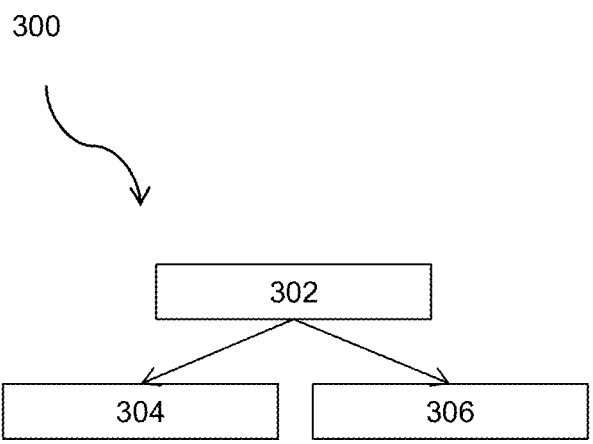
FIG. 3 shows a method of generating target cell variables for training.

Referring now to FIG. 3, shown therein is a method of generating target cell variables for training. During training of a neural network, a family of gradient-following procedures are performed where weights ("θ") of a neural network are changed according to the gradient of a cost function evaluated using the prediction and the target in a training dataset. To construct the training procedure, the measured cell variable to be modeled is represented in a mathematical form, also referred to as the 'target' in a dataset. For example, in predicting the percent-spliced-in values ("PSI"), two distinct forms could be provided, the expected PSI and a discretized version of PSI.

To compute these targets, at block 302, the biological measurements such as RNA-Seq datasets are processed to produce a posterior probability distribution p of PSI, using methods such as cufflinks and the bootstrap binomial model.

With posterior probability of PSI, at block 304, the expected PSI can be computed by an exact evaluation or an approximation to the following integral: $E(\psi)=\int_\psi \psi p(\psi) d\psi$. The result is a scalar value between 0 and 1. A regression model to predict the expected PSI can be trained, with the cost function being squared loss function or the cross-entropy based on a binomial distribution with $E(\psi)$ as the probability of success. In addition to the expected PSI, a discretized version of PSI may also be determined at block 306, which is defined by the probability mass of PSI in k predefined bins with boundaries ranging between 0 and 1. For example, using k=3 bins with a uniform bin width, we arrive at the 'low, mid, high' (LMH) formulation of PSI, which we also call a 'splicing pattern'. With this formulation, $p(\psi)$ is discretized to three probabilities $\{p_{low}, p_{mid}, p_{high}\}$ for use during training. In particular, $p_{low}$ is equal to the probability that PSI is between 0 and ⅓: $p_{low}=\int_0^{1/3} p(\psi) d_\psi$. For the discretized splicing patterns, the cross entropy cost function can be used for a classification model.

Though the preparation of training targets according to method 300 may be different for different cell variables, the system architecture applied may be the same or similar.

Referring now to FIGS. 4 to 9, shown therein are example DNN architectures for CVPs that predicts splicing levels ($\Psi$).

Though the figures depict possible architecture embodiments, the number of hidden layers and the number of processing units in each layer can range widely and may be determined by hand, using data or using other information;

In an embodiment, the nodes of the DNN are fully connected, where each connection is parameterized by a real-valued weight $\theta$. The DNN has multiple layers of non-linearity consisting of hidden units. The output activation a of each hidden unit v in layer l processes a sum of weighted outputs from the previous layer, using a non-linear function f:

$$a_v^l = f(\Sigma_m^{M^{l-1}} \theta_{v,m}^l a_m^{l-1})$$

where $M^l$ represents the number of hidden units in layer l, and $a_0$ and $M_0$ are the input into the model and its dimensionality, respectively. Different activation functions for the hidden units can be used, such as the TANH function, SIGMOID, and the rectified linear unit (RELU).

Figure 4:
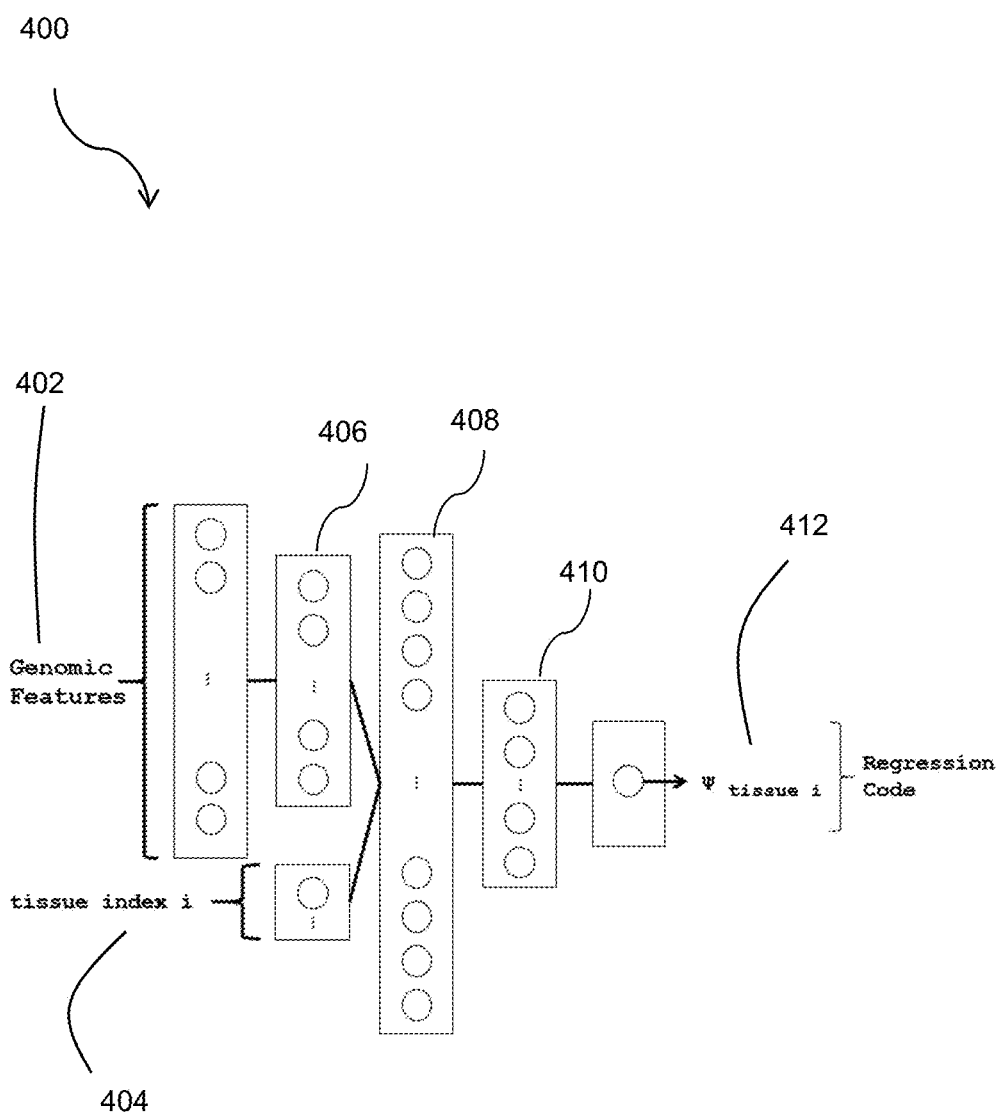
FIG. 4 shows an example deep neural network architecture for a cell variable predictor that predicts splicing levels.

Referring now to FIG. 4, shown therein is an example architecture 400 of a deep neural network that predicts alternative splicing inclusion levels in a single tissue type i, where the inclusion level is represented by a real-valued number $\Psi_i$.

Inputs into the first hidden layer 406 consist of genomic features 402 describing a genomic region; these features may include binding specificities of RNA- and DNA-binding proteins, RNA secondary structures, nucleosome positions, position-specific frequencies of short nucleotide sequences, and many others. To improve learning, the features can be normalized by the maximum of the absolute value across all training examples. The purpose of the first hidden layer is to reduce the dimensionality of the input and learn a better representation of the feature space.

The identity of conditions (e.g., tissues) 404, which consists of a 1-of-T binary variables where T represent the number of conditions, are then appended to the vector of outputs of the first hidden layer, together forming the input into the second hidden layer 408. A third hidden layer 410, or additional hidden layers may be included if found to be necessary to improve generalization performance.

In an embodiment, the final output 412 may be a regression model that predicts the expected PSI.

Figure 5:
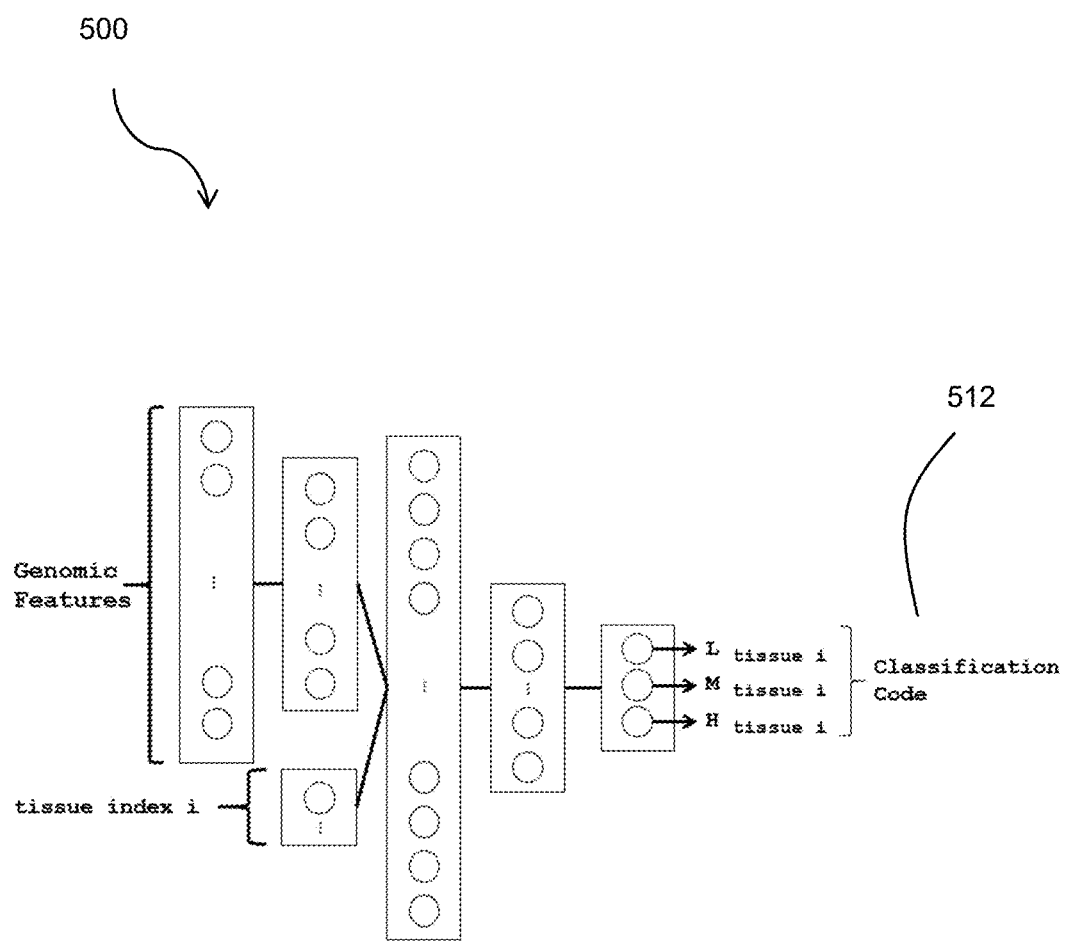
FIG. 5 shows a further example deep neural network architecture for a cell variable predictor that predicts splicing levels.

Referring now to FIG. 5, in another embodiment, the discretized PSI may be predicted by a classification model 512. FIG. 5 shows an example architecture 500 of a deep neural network that predicts alternative splicing inclusion levels in a single tissue type i, where the probability mass function over inclusion levels is represented by a k-valued vector, depicted here with k=3 values labeled (Low, Medium, High).

Figure 6:
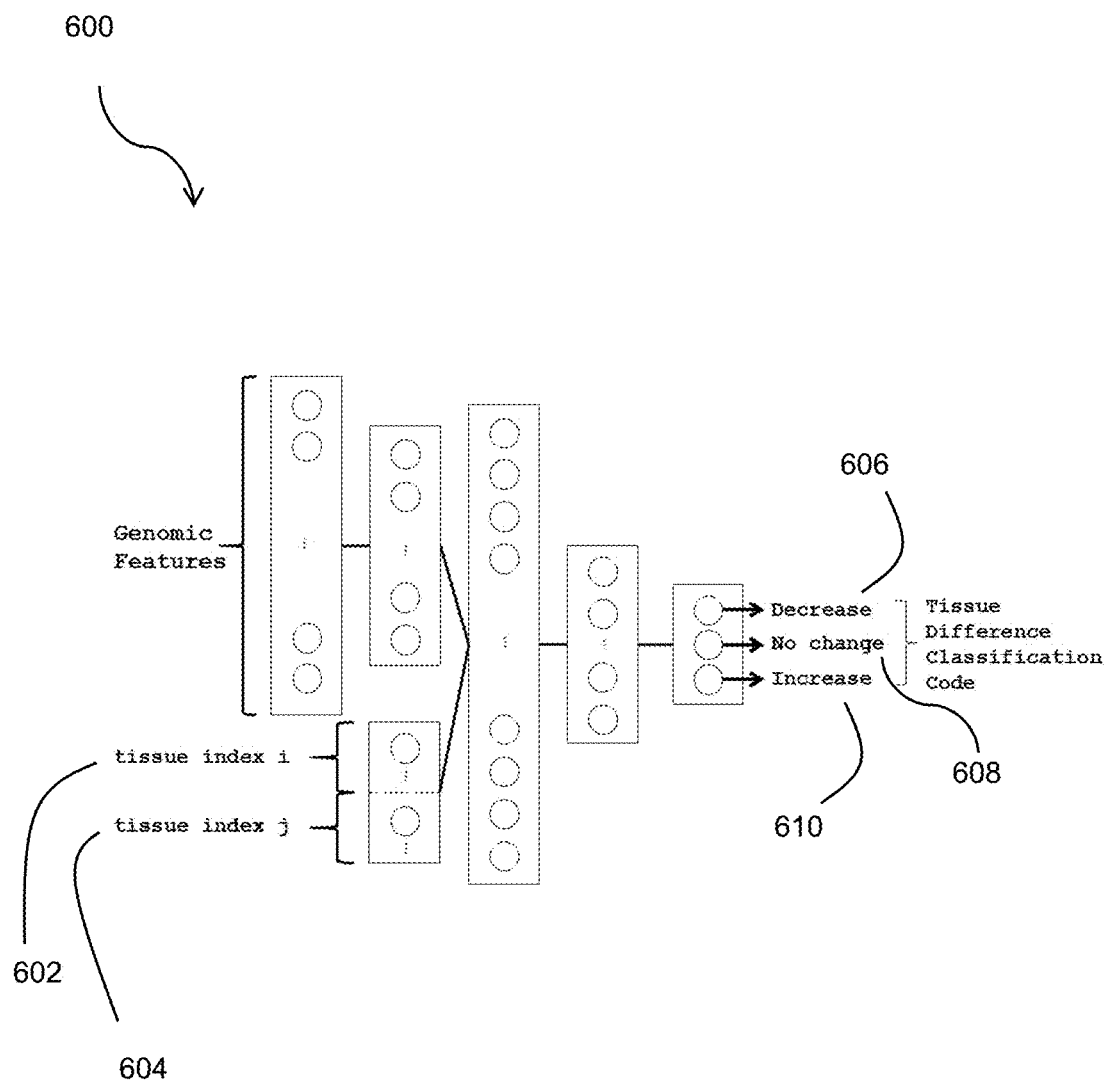
FIG. 6 shows yet a further example deep neural network architecture for a cell variable predictor that predicts splicing levels.

Referring now to FIG. 6, alternatively, the DNN can predict the difference in PSI ($\Delta$PSI) between two conditions for a particular exon. FIG. 6 shows an example architecture 600 of a deep neural network that predicts the difference between the alternative splicing inclusion levels of two tissue types (conditions) i 602 and j 604. Here, instead of one tissue as input, two different tissues can be supplied to the inputs.

Further, three classes can be generated, called decreased inclusion 606, no change 608, and increased inclusion 610, which can be similarly generated, but from the $\Delta$PSI distributions. An interval can be chosen that more finely differentiates tissue-specific alternative splicing for this task, where a difference of greater than 0.15 could be labeled as a change in PSI levels. The probability mass could be summed over the intervals of −1 to −0.15 for decreased inclusion, −0.15 to 0.15 for no change, and 0.15 to 1 for increased inclusion.

Figure 7:
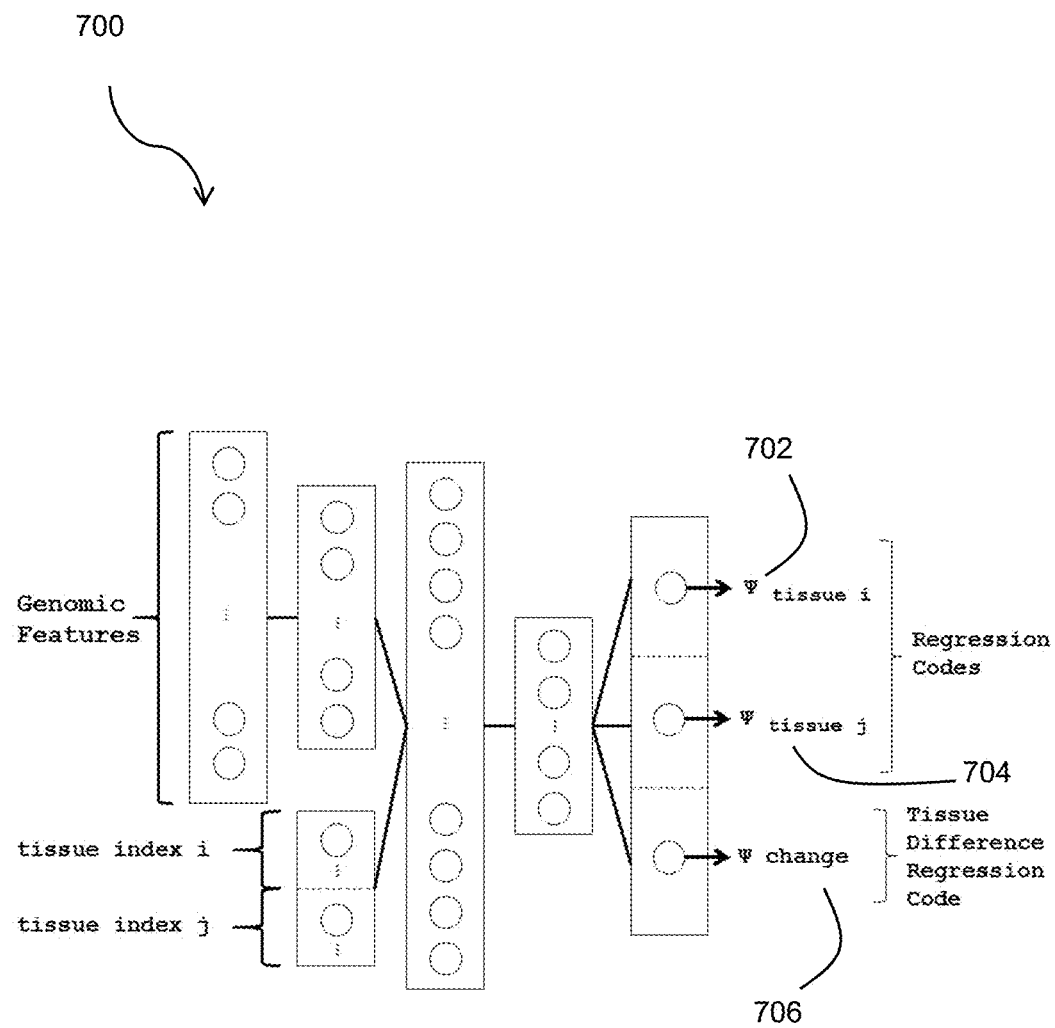
FIG. 7 shows yet a further example deep neural network architecture for a cell variable predictor that predicts splicing levels.

Referring now to FIG. 7, shown therein is an example architecture 700 of a deep neural network that predicts the alternative splicing inclusion levels of two tissue types i and j, where the inclusion levels are represented by real-valued numbers $\Psi_i$ 702 and $\Psi_j$ 704 and the difference in alternative splicing inclusion levels between the two tissue types 706 is also represented by a real-valued number.

In embodiments, the classification, regression, and tissue difference codes may be trained jointly. The benefit is to reuse the same hidden representations learned by the model, and for each learning task to improve the performance of another.

Figure 8:
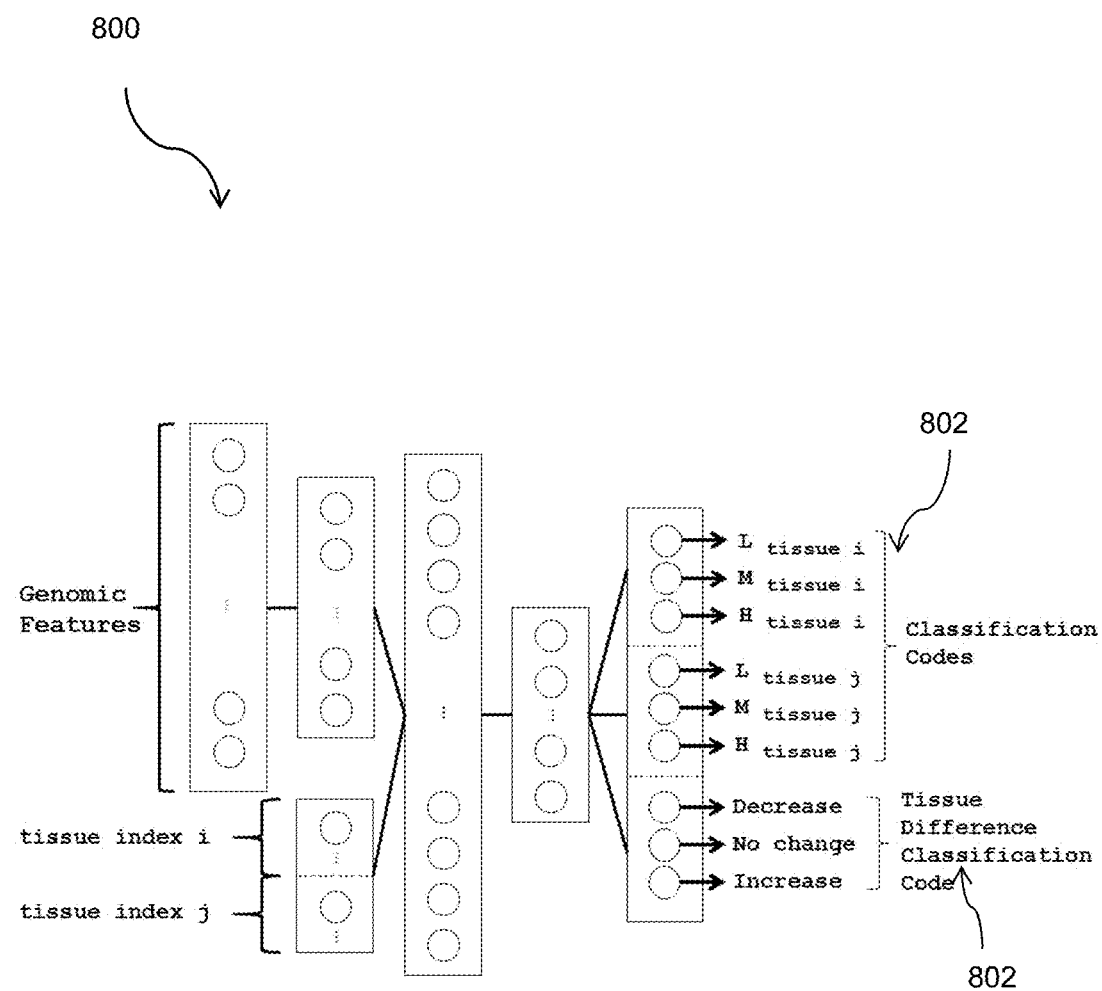
FIG. 8 shows yet a further example deep neural network architecture for a cell variable predictor that predicts splicing levels.

Referring now to FIG. 8, shown therein is an example architecture 800 of a deep neural network that predicts the difference between the alternative splicing inclusion levels of two tissue types i and j, where the probability mass function over inclusion levels is represented by a k-valued vector, depicted here with k=3 values labeled (Low, Medium, High) 802 and the probability mass function over inclusion level differences is represented by a d-valued vector, here depicted with d=3 values labeled (Decrease, No Change, Increase) 804.

Figure 9:
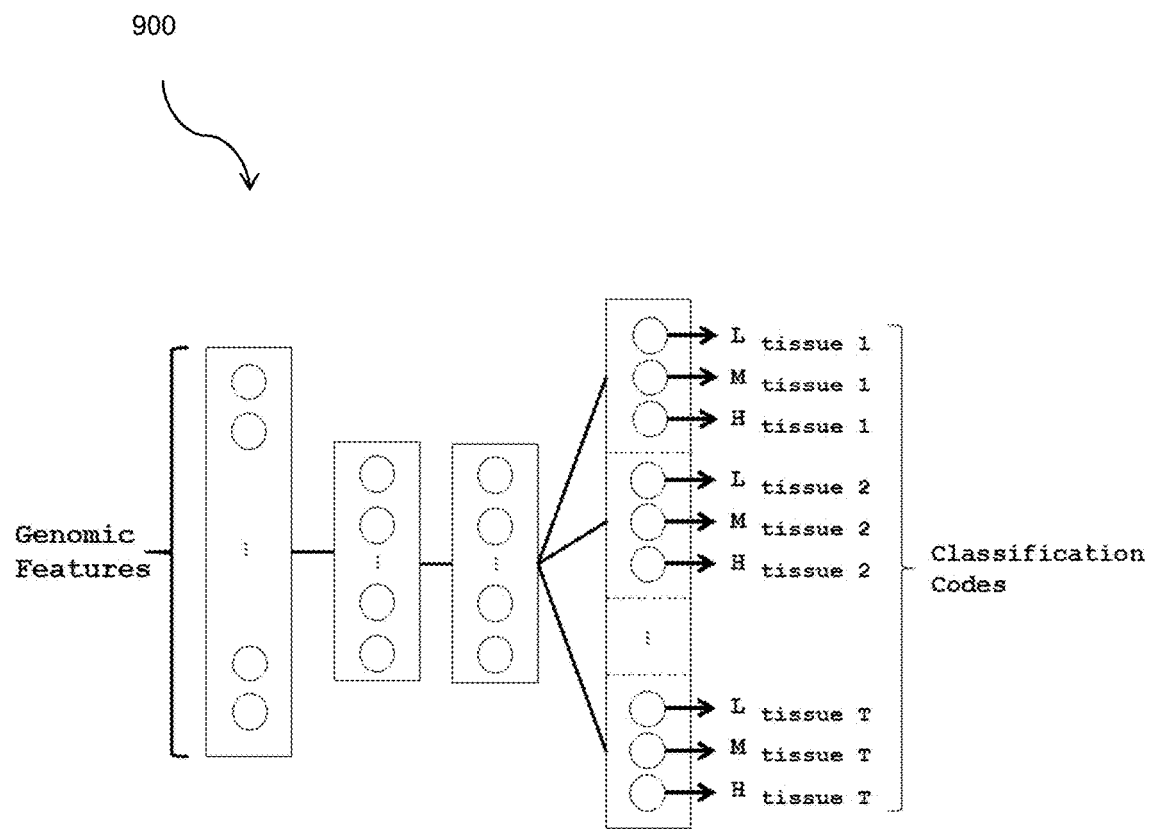
FIG. 9 shows yet a further example deep neural network architecture for a cell variable predictor that predicts splicing levels.

Referring now to FIG. 9, shown therein is an example architecture 900 of a deep neural network that predicts alternative splicing inclusion levels in T tissue types, where the probability mass function over inclusion levels is represented by a k-valued vector, depicted here with k=3 values labeled (Low, Medium, High). Accordingly, multiple tissues may be trained as different predictors via multitask learning. The learned representation from features may be shared across all tissues. FIG. 9 shows an example architecture of such system.

Figure 10:
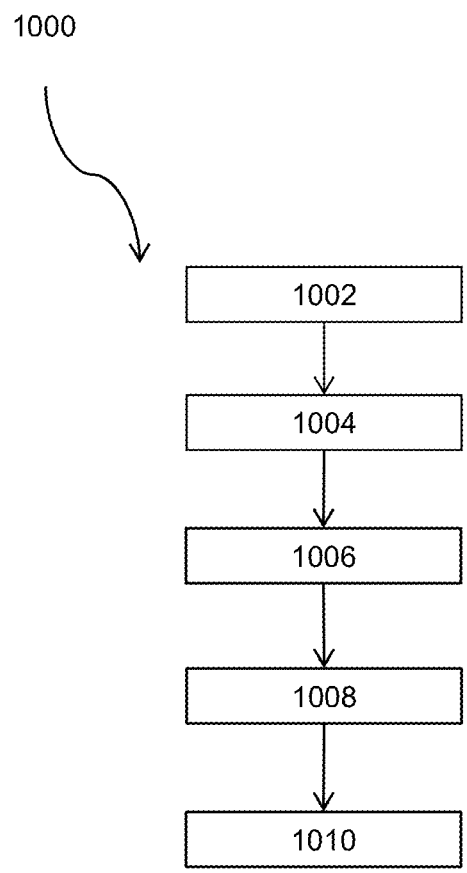
FIG. 10 shows a method for training cell variable predictors.

Training of the systems will now be described with reference to FIGS. 10 to 12. Referring now to FIG. 10, shown therein is a method 1000 for training the cell variable predictors of the systems described above. At block 1002, the first hidden layer can be trained using an autoencoder to reduce the dimensionality of the feature space in an unsupervised manner. An autoencoder is trained by supplying the input through a non-linear hidden layer, and reconstructing the input, with tied weights going into and out of the hidden layer. Alternatively, the weights can be untied. This method of pretraining the network may initialize learning near a good local minimum. An autoencoder may be used instead of other dimensionality reduction techniques like principal component analysis, because it naturally fits into the CVP's architecture, and that a non-linear technique may discover a better and more compact representation of the features. At block 1004, in the second stage of training, the weights from the input layer to the first hidden layer (learned from the autoencoder) are fixed, and the inputs corresponding to tissues are appended. A one-hot encoding representation may be used, such that specifying a tissue for a particular training example can take the form [0 1 0 0 0] to denote the second tissue out of 5 possible types. At block 1006, the reduced feature set and tissue variables become input into the second hidden layer. At block 1008, the weights connected to the second hidden layer and the final hidden layer of the CVP are then trained together in a supervised manner, with targets being the expected value of PSI, the discretized version of PSI, the expected value of ΔPSI, and/or the discretized version of ΔPSI, depending on architecture. At block 1010, after training these final two layers, weights from all layers of the CVP may be fine-tuned by backpropagation.

In an alternate embodiment, the autoencoder may be omitted altogether, and all weights of neural network may be trained at once.

In one embodiment, the targets consist of (1) PSI for each of the two tissues, and (2) ΔPSI between the two tissues. Given a particular exon and N possible tissue types, N×N training examples can be constructed. This construction has redundancy in that it generates examples where both tissues are the same in the input to teach the model that it should predict no change for ΔPSI given identical tissue indices. Additionally, if the tissues are swapped in the input, a previously increased inclusion label should become decreased inclusion. The same rationale extends to the LMH classifier. Generating these additional examples is one method to incorporate this knowledge without explicitly specifying it in the model architecture.

A threshold can be applied to exclude examples from training if the total number RNA-Seq junction is below a number, such as 10, to remove low signal training examples.

In some of the embodiments, multiple tasks may be trained together. Since each of these tasks might learn at different rates, learning rates may be allowed to differ. This is to prevent one task from overfitting too soon and negatively affecting the performance of another task before the complete model is fully trained. This may be implemented by having different learning rates for the weights between the connections of the last hidden layer and the functions used for classification or regression for each task.

To train and test CVPs of the systems described herein, data may be split into folds at random for cross validation, such as five approximately equal folds. Each fold may contain a unique set of genetic information, such as exons that are not found in any of the other folds. Where five folds are provided, three of the folds could be used for training, one used for validation, and one held out for testing. Training can be performed for a fixed number of epochs and hyperparameters can be selected that give optimal area under curve ("AUC") performance or data likelihood on the validation data. The model can then be re-trained using the selected hyperparameters with both the training and validation data. Multiple models can be trained this way from the different folds of data. Predictions from the models on their corresponding test set can then be used to evaluate the code's performance. To estimate the confidence intervals, the data can be randomly partitioned, and the above training procedure can be repeated.

The CVP's processing unit weights may be initialized with small random values sampled from a zero-mean Gaussian distribution. Alternatively it may be initialized with small random values with a zero-mean uniform distribution. Learning may be performed with stochastic gradient descent with momentum and dropout, where mini-batches are constructed as described below. An L1 weight penalty may be included in the cost function to improve the model performance by disconnecting features deemed to be not useful by the predictor. The model's weights may updated after each mini-batch.

Figure 11:
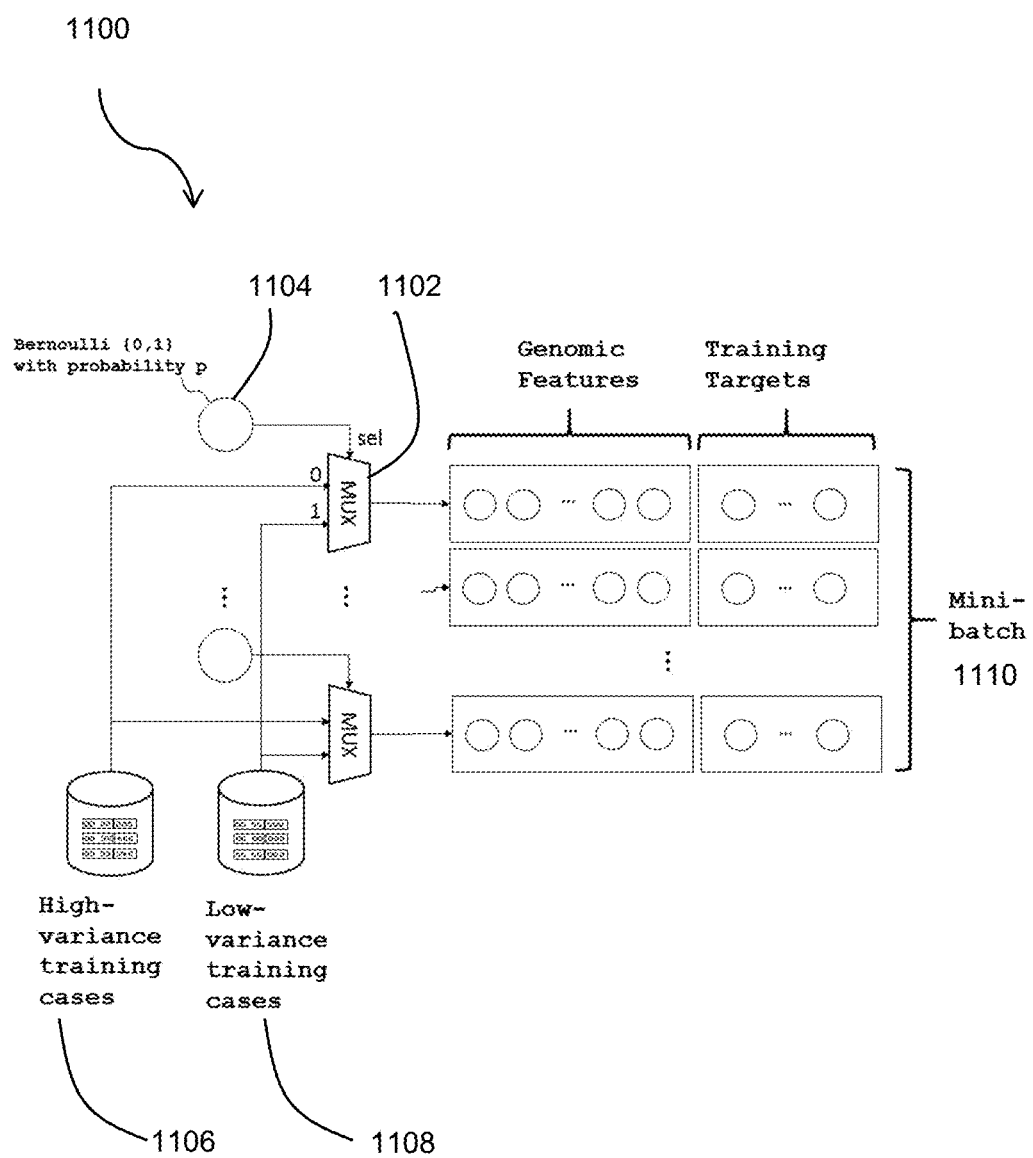
FIG. 11 shows a system to perform non-uniform sampling of training cases for determining a mini-batch for training a deep neural network.

Referring now to FIG. 11, shown therein is a system to perform non-uniform sampling of training cases for creating a mini-batch for training a deep neural network.

To promote neural networks to better discover patterns in the inputs that help to distinguish tissue types or genomic features, a system is provided for biasing the distribution of training events in the mini-batches. The system comprises training cases separated into "high-variance" cases and "low-variance" cases. The set of high-variance training cases is thus selected by thresholding each case's variance across tissue types or genomic features. In the illustrated embodiment the "high-variance" cases are provided in a database 1106, and the "low-variance" cases are provided in a database 1108. The system further comprises switches 1104 and multiplexers 1102. In use, each row of a mini-batch 1110 is sampled either from a list of high- or low-variance training cases, depending on a probabilistic {0, 1} switch value. The resulting mini-batch of genomic features and corresponding cell variable targets can be used for training, such as for training the architectures in FIGS. 6 and 7.

Figure 12:
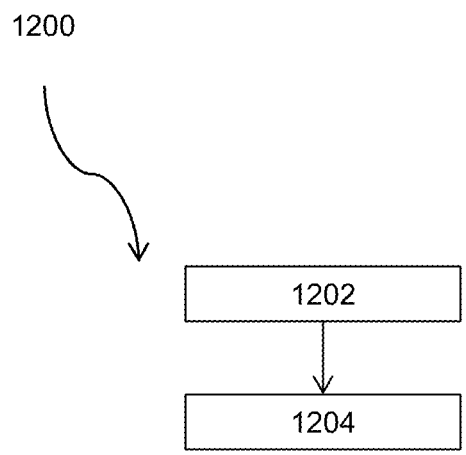
FIG. 12 shows a method for training cell variable predictors for ensuring a consistent backpropagation signal that updates the weights connected to tissue inputs and biases learning towards the event with large tissue variability early on before overfitting occurs.

Referring now to FIG. 12, shown therein is a method for training cell variable predictors for ensuring a consistent backpropagation signal that updates the weights connected to tissue inputs and biases learning towards the event with large tissue variability early on before overfitting occurs. According to a method 1200, at block 1202, all training cases are separated into a database of "high-variance" cases and a database of "low-variance" cases, where the variance of each training case is measured as "variance of the Ψ training targets across tissue types" and the threshold for separating high/low is any pre-determined constant. At block 1204, all events that exhibit large tissue variability are selected, and mini-batches are constructed based only on these events. At each training epoch, training cases can be further sampled (with or without replacement) from the larger pool of events with low tissue variability, of some pre-determined or randomized size typically smaller than equal to one fifth of the mini-batch size. A purpose of method 1200 is to have a consistent backpropagation signal that updates the weights connected to the tissue inputs and bias learning towards the event with large tissue variability early on before overfitting occurs. As training progresses, the splicing pattern of the events with low tissue variability is also learned. This arrangement effectively gives the events with large tissue variability greater importance (i.e. more weight) during optimization. This may be beneficial to improve the models' tissue specificity.

With the above methods for training, techniques to reduce overfitting can be applied to the system to provide an embodiment of a CVP with dropout. Along with the use of GPUs, CVPs comprising of deep neural networks may be a competitive technique for conducting learning and prediction on biological datasets, with the advantage that they can be trained quickly, have enough capacity to model complex relationships, and scale well with the number of hidden variables and volume of data, making them potentially highly suitable for 'omic' datasets.

Additionally, the performance of a CVP depends on a good set of hyperparameters. Instead of conducting a grid search over the hyperparameter space, Bayesian frameworks can be used to automatically select a model's hyperparameters. These methods use a Gaussian Process to search for a joint setting of hyperparameters that optimize a process's performance on validation data. It uses the performance measures from previous experiments to decide which hyperparameters to try next, taking into account the trade-off between exploration and exploitation. This method eliminates many of the human judgments involved with hyperparameter optimization and reduces the time required to find such hyperparameters. Alternatively, randomized hyperparameter search can be performed, where the hyperparameters to be optimized is sampled from a uniform distribution. These methods require only the search range of hyperparameter values to be specified, as well as how long to run the optimization for.

Figure 13:
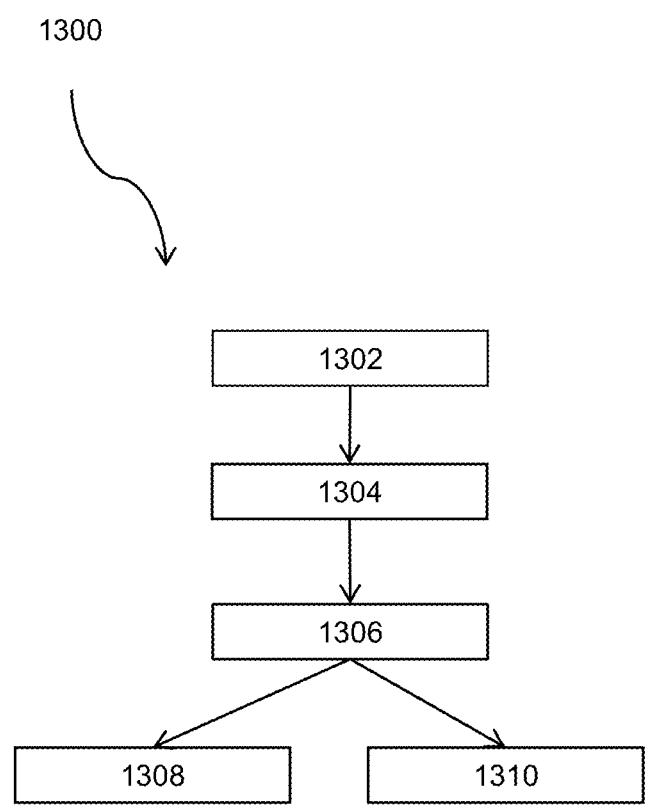
FIG. 13 shows a method for using the outputs of the CVP for scoring, classifying and prioritizing genetic variants.

In the following paragraphs, methods for using the outputs of the CVP for scoring, classifying and prioritizing genetic variants (with reference to FIG. 13); for scoring variants by associating cell variable changes with those of other variants (with reference to FIG. 14); and for interpreting which genetic features account for variant-induced cell variable changes (with reference to FIGS. 15 to 18), will be described.

The systems described above can be used to compute a set of condition-specific scores for how deleterious a variant is. For instance, a variant may be found to have a high deleteriousness score in brain tissue, but not in liver tissue. In this way the condition-specific cell variables computed as described above can be used to compute condition-specific deleteriousness scores. To classify variants as pathogenic, likely pathogenic, unknown significance (VUS), likely benign or benign, and to prioritize or rank a set of variants, these sets of scores can be combined.

According to a method 1300, to quantify the effect of a SNV (single nucleotide variation) or a combination of mutations (called in general a variant) using a CVP, at block 1302, a pair of feature vectors are constructed corresponding to the reference sequence and the variant sequence. Due to the mutation, these genomic feature vectors will be different, but without a further CVP it may not be possible to predict whether those differences will result in any change in phenotype. At block 1304, the predictive system is therefore used to compute both the reference cell variable value and the mutant cell variable value for each condition, using these two distinct feature vectors. After that, at block 1306, a distance function that combines the reference and the mutant predictions can be used to produce a single score for each condition, which summarizes the magnitude of predicted effect induced by the mutations. Because large change of cell variables is likely to cause diseases, without further information about a particular diseases and a particular cell variable, high scoring mutations are assumed to cause diseases.

Examples of distance functions are the expected difference, Kullback-Leibler divergence, and variation distance. In the following, we describe each of these distance functions in detail using a LMH splicing predictor as an example.

The expected difference represents the absolute value of the difference induced by the mutation in the expected value of a cell variable. For an LMH PSI predictor, the predicted reference splicing patterns in $\{p_{low}^{wt}, p_{mid}^{wt}, p_{high}^{wt}\}$ and the predicted mutant splicing patterns $\{p_{low}^{mut}, p_{mid}^{mut}, p_{high}^{mut}\}$ are computed using the reference and mutant feature vectors as inputs. Then, the expected value of the predicted cell variable with and without the mutation is computed, denoted as $\psi_{wt}$ and $\psi_{mut}$. The expected value is a weighted average of the PSI values corresponding to the center of the bins used to define the splicing pattern. As described above, if three bins are used with uniform spacing, reference PSI is computed by $\psi_{wt} = \frac{1}{6} p_{low}^{wt} + \frac{1}{2} p_{mid}^{wt} + \frac{5}{6} p_{high}^{wt}$. In the same way, mutant PSI is computed by $\psi_{mut} = \frac{1}{6} p_{low}^{mut} + \frac{1}{2} p_{mid}^{mut} + \frac{5}{6} p_{high}^{mut}$. The final score is the absolute difference between the expected PSI: $s = |\psi_{mut} - \psi_{wt}|$. This can be combined across conditions, by computing the maximum absolute difference across conditions.

Kullback-Leibler (KL) divergence is an information theoretic measure of difference between probability distributions P and Q:

$$D_{KL}(P, Q) = \Sigma_i P(i) \log \frac{P(i)}{Q(i)}.$$

Due to the asymmetric nature of the KL divergence, either $s = D_{KL}(P_{wt}, P_{mut})$ or $S = D_{KL}(P_{mut}, P_{wt})$ can be used as the distance measure. The KL divergence can be computed for each condition and the sum (or average) KL divergence can be computed across conditions, or the maximum KL divergence can be computed across tissues.

The variation distance is another measure of difference between probability distributions. It is the sum of absolute value of the predicted probabilities. In the LMH splicing predictor example, $$s = \frac{1}{2} \Sigma_{s \in \{low, mid, high\}} |p_s^{mut} - p_s^{wt}|.$$

Again, this can be computed for each condition and then the sum or maximum can be taken across conditions.

Once the score of a variant has been computed at block 1306, at block 1308 the score can be thresholded and/or combined with other information to classify the variant as pathogenic, likely pathogenic, unknown significance (VUS), likely benign or benign.

Further, at block 1310, given a set of variants, the score of every variant can be computed and the set of variants can be reordered so that the highest-scoring (most deleterious) variants are at the top of the list and the lowest-scoring variants are at the bottom of the list.

Figure 14:
FIG. 14 shows a method for scoring variants by associating cell variable changes with those of other variants.

Referring now to FIG. 14, a method 1400 is shown for scoring, classifying and prioritizing variants. The method 1400 comprises by, at block 1402, associating the cell variable changes of variants with those of other variants with known function. For instance, suppose the system 100 determines that a variant that has never been seen before causes a change in a particular cell variable, say the cassette splicing level of a specific exon. Suppose a nearby variant whose disease function is well-characterized causes a similar change in the exact same cell variable, e.g., the splicing level of the same exon. Since mutations act by changing cellular chemistry, such as the splicing level of the exon, it can be inferred that the unknown variant likely has the same functional impact as the known variant. The system can ascertain the 'distance' between two variants in this fashion using a variety of different measures. Because the system computes variant-induced changes in a cell variable for different conditions, this information can be used to more accurately associate variants with one another. For example, two variants that induce a similar cell variable change in brain tissue would be associated more strongly than two variants that induce similar cell variable changes, but in different tissues.

Unlike many existing systems, the methods and systems described here can be used to score, classify, prioritize and interpret a variant in the context of different reference sequences. For instance, when a child's variant is compared to a reference sequence obtained from the reference human genome, the variant may have a high score, but when the same variant is compared to the reference sequences obtained from his or her unaffected parents, the variant may have a low score, indicating that the variant is likely not the cause of the disease. In contrast, if the child's variant is found to have a high score when it is compared to the reference sequences obtained from his or her parents, then it is more likely to be the cause of the disease. Another circumstance in which different reference sequences arise is when the variant may be present in more than one transcript, which can occur because transcription occurs bidirectionally in the genome, there may be alternative transcription start sites, there may be alternative splicing, and for other reasons.

Referring now to FIGS. 15 to 19, methods will now be described to identify the impact of features (which may include nucleotides) on a cell variable CVP prediction.

It can be useful to determine why a variant changes a cell variable and leads to disease. A variant leads to a change in DNA/RNA sequence and/or a change in the DNA/RNA features extracted from the sequence. However, which particular changes in the sequence or features are important. An SNV may change more than one feature (e.g., a protein binding site and RNA secondary structure), but because of contextual dependence only some of the affected features play an important role.

To ascertain this, the system 100 can determine which inputs (nucleotides or DNA/RNA features) are responsible for changes in cell variables. In other words, it is useful to know how important a feature is overall for making a specific prediction, and it is also useful to know in what way the feature contributes to the prediction (positively or negatively).

Figure 15:
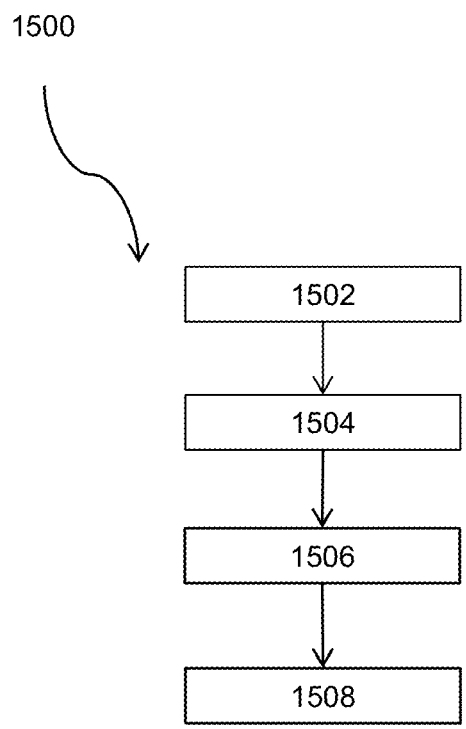
FIG. 15 shows a method for interpreting which genetic features account for variant-induced cell variable changes.

Referring now to FIG. 15, a first method 1500 to identify the impact of features on a cell variable CVP prediction works by computing, at block 1502, the features for the sequence containing the variant and the features for the sequence that does not have the variant. At block 1504, both feature vectors are fed into the cell variable predictor to obtain the two sets of condition-specific cell variables. At block 1506, a single feature from the variant sequence is copied into the corresponding feature in the non-variant sequence and the system is used to compute the set of condition-specific cell variables. At block 1508, this is repeated for all features and the feature that produces the set of condition-specific cell variables that is most similar to the set of condition-specific cell variables for the variant sequence is identified. This approach can be extended to test a set of pairs of features or a set of arbitrary combinations of features.

Figure 16:
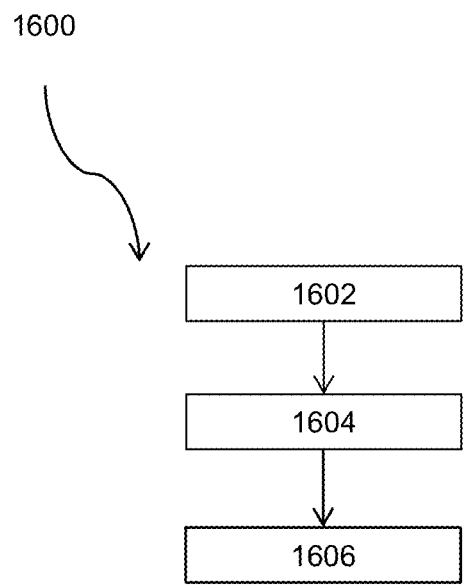
FIG. 16 shows a further method for interpreting which genetic features account for variant-induced cell variable changes.

Referring now to FIG. 16, a second method 1600 to identify the impact of features on a cell variable CVP prediction evaluates the impact of a subset $S \subseteq \{1, \ldots n\}$ of input features $x=(x_1, \ldots, x_n)$ on the corresponding cell variable prediction $z=f(x)$. The method consists of, at block 1602, constructing a new set of input features $\hat{x}=(\hat{x}_1, \ldots, \hat{x}_n)$ where for each feature index $i \in S$ in the subset the value $\hat{x}_i$ has been replaced with the median value of $x_i$ across the training dataset. At block 1604, this new feature vector is then sent through the cell variable prediction system in question, resulting in a new prediction $\hat{z}=f(\hat{x})$. For a splicing cell variable predictor, this entails replacing genomic feature $x_i$ with its median value across all events (all exons) in the training set. The impact of feature subsets of the same size are comparable, including all cases when $|S|=1$. Among comparable feature subsets, those that correspond to the largest decrease in performance may be deemed to have high impact. At block 1606, the overall importance of a feature (as opposed to its importance for a specific training or test case) with regard to a particular dataset (e.g. a training or test set) can be determined as the average or median of all its impact scores across all cases in that dataset.

Figure 17:
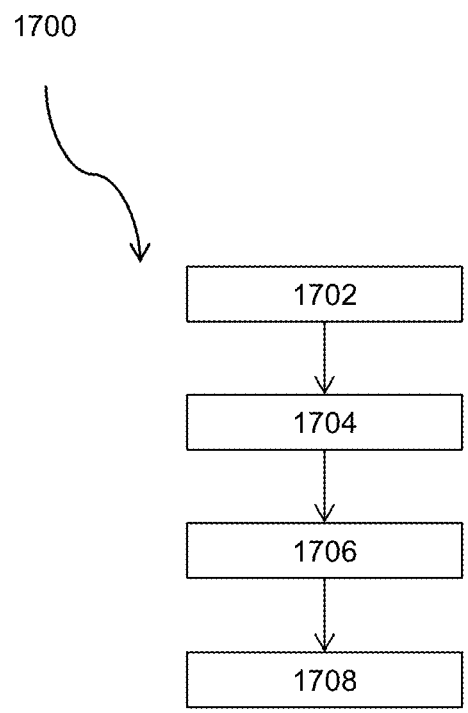
FIG. 17 shows a further method for interpreting which genetic features account for variant-induced cell variable changes.

Referring now to FIG. 17, a third method 1700 is described to identify the impact of features on a cell variable CVP prediction. At block 1702, an example from the dataset is given as input to the trained model and forward propagated through a CVP comprising of a neural network to generate an output. At block 1704, the target is modified to a different value compared to the predicted output; for example, in classification, the class label would be modified so that it differs from the prediction. At block 1706, the error signal is backpropagated to the inputs. The resulting signal describes how much each input feature needs to change in order to make the modified prediction, as well as the direction. The computation is extremely quick, as it only requires a single forward and backward pass through the CVP, and all examples can be calculated in parallel. Features that need to be changed the most are deemed to be important. At block 1708, the overall importance of a feature (as opposed to its importance for a specific training or test case) with regards to a particular dataset (e.g. a training or test set) can be determined as the average or median of amount of change across all cases in that dataset. The benefit of this approach compared to the first is it can model how multiple features operate simultaneously.

Figure 18:
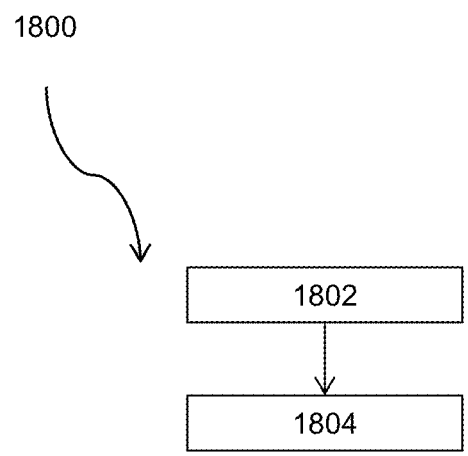
FIG. 18 shows a method to generate a visualization for tissue-specific feature importance.

Referring now to FIG. 18, a complementary method 1800 based on the method of 1700 to analyze a CVP is to see how features are used in a tissue-specific manner. At block 1802, this extension simply receives examples from the dataset corresponding to particular tissues, and, at block 1804, performs the procedure as described above [110]. In cases where the cell variable predictor is tissue-specific (e.g. FIGS. 4-9) this procedure yields tissue-specific feature importance information.

Figure 19:
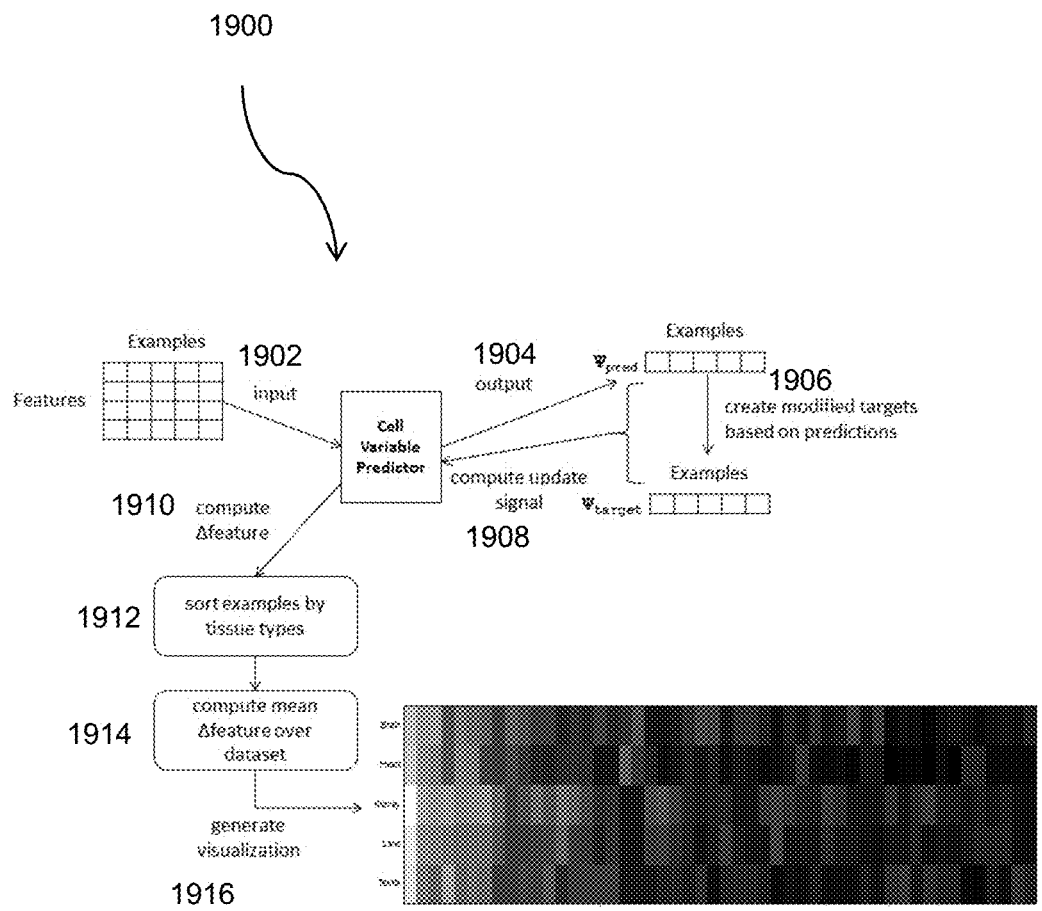
FIG. 19 shows a detailed illustration of the method to generate a visualization for tissue-specific feature importance.

Referring now to FIG. 19, shown therein is a detailed illustration of a method 1900 to generate a visualization for tissue-specific feature importance based on the method described in 1700 and 1800. At block 1902, input comprising examples from a dataset corresponding to a particular tissue is provided to the CVP. At block 1904, tissue-specific cell variable predictions are provided by the CVP. At block 1906, targets are constructed based on the cell value predictions, such that there is a mismatch between the prediction and the target. At block 1908, an update signal is computed which describes how the weights of the connection need to change to make the prediction match the target. At block 1910, an update signal backpropagated to the input, $\Delta$feature, is further computed. At block 1912, examples from the dataset are sorted by tissue types. At block 1914, the overall importance of features for each tissue is computed by taking the mean of the magnitude of the update signal over the entire dataset. At block 1916, a visualization is generated, where the importance of each feature is colored accordingly for each tissue.

The systems and methods described here can also be used to determine whether a therapy reverses the effect of a variant on a pertinent cell variable. For example, an SNV within an intron may cause a decrease in the cell variable that corresponds to the inclusion level of a nearby exon, but an oligonucleotide therapy that targets the same region as the SNV or a different one may cause the cell variable (inclusion level) to rise to its original level. Or, a DNA editing system such as CRISPR-Cas9 may be used to edit the DNA, adding, remove or changing a sequence such that the cell variable (inclusion level) of the exon rises to its original level. If the method described here is applied to a variant and a reference sequence obtained from the reference genome or an unaffected family member, and the cell variable is found to change by a certain amount, or if the cell variable has been measured to change by a certain amount, the following technique can be used to evaluate putative therapies to see if they correct the change. In the case of therapies that target the variant sequence, such as by protein-DNA or protein-RNA binding or by oligonucleotide hybridization, the effect of the therapy on the variant can be computed using the CVP, where the reference is taken to be the variant sequence and the "variant sequence" is now taken to be the variant sequence modified to account for the effect of the therapy. If the therapy targets a subsequence of the variant, that subsequence may be, in silico, modified by randomly changing the nucleotides, setting them all to a particular value, or some other method. Alternatively or additionally, when features are extracted from the modified sequence, features that overlap, fully or partially, with the targeted subsequence may be set to values that reflect absence of the feature. The reference (the original variant) and the modified variant are then fed into the CVP and the change in the cell variable is computed. This is repeated with a wide range of therapies, and the efficacy of each therapy can be determined by how much the therapy-induced change in the cell variable corrects for the original variant-induced change. In the case of a DNA editing system, such as CRISPR-Cas9, the procedure is even more straightforward. The reference is taken to be the original variant, and the variant is taken to be the edited version of the variant. The output of the CVP then indicates by how much the cell variable will change because of the editing.

Thus, what has been provided is, essentially, a system and method for computing variant-induced changes in one more condition-specific cell variables. An exemplary method comprises computing a set of features from the DNA or RNA sequence containing the variant, applying a network of at least two layers of processing units (the deep neural network) to the variant features to compute the one or more condition-specific variant cell variables, computing a set of features from a reference DNA or RNA sequence, applying the deep network to the reference features to compute the one or more condition-specific reference cell variables, and computing the variant-induced changes in the one or more condition-specific cell variables by comparing the one or more condition-specific reference cell variables to the one or more condition-specific variant cell variables. In embodiments, the number of condition-specific cell variables is at least two.

The deep neural network may be trained using a dataset of examples, where each example is a measured DNA or RNA sequence and a corresponding set of measured values of the condition-specific cell variables, one for each condition, and where the condition-specific cell variables are not normalized using a baseline that is determined by combining the condition-specific cell variables across two or more conditions.

The set of features may include a binary matrix with 4 rows and a number of columns equal to the length of the DNA or RNA sequence and where each column contains a single '1' and three '0's and where the row in which each '1' occurs indicates the nucleotide at the corresponding position in the DNA or RNA sequence. The set of features includes a set of features may be computed using the recognition path of an autoencoder that is applied to the binary matrix. The autoencoder may be trained using a dataset of binary matrices computed using a set of DNA or RNA sequences of fixed length. The set of features may also include real and binary features derived from the DNA or RNA sequence.

At least part of the deep network may be configured to form a convolutional network and/or recurrent network. Part of the deep network that is a recurrent network may be configured to use of long-term short-term memory.

The deep neural network may be trained using a dataset of feature vectors extracted from DNA or RNA and a corresponding set of measured values of cell variables. The training method may adjust the parameters of the deep neural network so as to minimize the sum of the error between the measured cell variables and the output of the deep neural network. The error may be the squared difference between the measured cell variable and the corresponding output of the neural network. The error may be the absolute difference between the measured cell variable and the corresponding output of the neural network. The error may be the Kullback-Leibler divergence between the measured cell variable and the corresponding output of the neural network. Stochastic gradient descent may be used to train the deep neural network.

Dropout may be used to train the deep neural network.

The hyperparameters of the deep neural network may be adjusted so as to minimize the error on a separate validation set.

The deep neural network may be trained using multitask learning, where the outputs of the deep neural network are comprised at least two of the following: a real-valued cell variable, a probability distribution over a discretized cell variable, a probability distribution over a real-valued cell variable, a difference between two real-valued cell variables, a probability distribution over a discretized difference between two real-valued cell variables, a probability distribution over the difference between two real-valued cell variables.

An input to the deep neural network may indicate the condition for which the cell variable is computed and the deep neural network is applied repeatedly to compute each condition-specific cell variable.

The output of the deep neural network may comprise one real value for each condition and the variant-induced change for each condition may be computed by subtracting the computed reference cell variable from the computed variant cell variable.

The output of the deep neural network may comprise a probability distribution over a discrete variable for each condition and the variant-induced change for each condition may be computed by summing the absolute difference between the computed probabilities for the reference cell variable and the variant cell variable.

The output of the deep neural network may comprise a probability distribution over a discrete variable for each condition and the variant-induced change for each condition may be computed using the Kullback-Leibler divergence between the computed probabilities for the reference cell variable and the variant cell variable.

The output of the deep neural network may comprise a probability distribution over a discrete variable for each condition and the variant-induced change for each condition may be computed by first computing the expected value of the reference cell variable and the variant cell variable, and then subtracting the expected value of the reference cell variable from the expected value of the variant cell variable.

The variant-induced changes in the one or more condition-specific cell variables may be combined to output a single numerical variant score. The variant score may be computed by summing the variant-induced changes across conditions. The variant score may be computed by summing the squares of the variant-induced changes across conditions. The variant score may be computed by summing the outputs of a nonlinear function that are computed by applying the nonlinear function to the variant-induced changes across conditions.

At least two variants and corresponding reference sequences may be independently processed to compute the variant-induced changes in one or more condition-specific cell variables for each variant and corresponding reference sequence. At least two variants and corresponding reference sequences may be independently processed to compute the variant score for each variant and corresponding reference sequence. The variant scores may be used to prioritize the variants by sorting them according to their scores. Thresholds may be applied to the score to classify the variant as deleterious or non-deleterious, or to classify the variant as pathogenic, likely pathogenic, unknown significance, likely benign or benign, or to classify the variant using any other discrete set of labels. A validation data consisting of variants, reference sequences, and labels may be used to compute the thresholds that minimize classification error. The scores may be combined with additional numerical information before the variants are sorted. The scores may be combined with additional numerical information before the thresholds are applied. The scores may be combined with additional numerical information before the thresholds are applied.

For one or more pairs of variants, the distance between the two variants in each pair may be computed by summing the output of a nonlinear function applied to the difference between the change in the condition-specific cell variable for the first variant and the change in the condition-specific cell variable for the second variant. The nonlinear function may be the square operation. The nonlinear function may be the absolute operation.

The deleteriousness label of an unknown variant may be determined by computing the distance of the variant to one or more variants of known deleteriousness and outputting the label or the score of the closest known variant. The deleteriousness value of an unknown variant may be determined by computing the distance of the variant to one or more variants of known deleteriousness and then computing the weighted average of their labels or scores, where the weights are nonlinear functions of the distances. Two or more unknown variants may be prioritized, by sorting them according to their deleteriousness values.

The mini-batches used during multitask training may be balanced so that the number of cases that exhibit a large difference is similar to the number of cases that exhibit a small difference.

The genetic variant may be a single nucleotide variant. The genetic variant may contain two or more distinct single nucleotide variants. The genetic variant may be a combination of substitutions, insertions and deletions and not be a single nucleotide variant. The genetic variant may be obtained by sequencing the DNA from a patient sample.

The reference sequence may be obtained by sequencing the DNA from a close relative of the patient. The reference sequence may be any DNA or RNA sequence and the variant sequence may be any DNA or RNA sequence, but where the reference sequence and the variant sequence are not identical.

The features may include position-dependent genetic features such as conservation.

The most explanatory feature may be determined by examining each feature in turn, and computing a feature-specific variant feature vector by copying the feature derived from the variant sequence onto the features derived from the reference sequence; using the deep neural network to compute the variant-induced changes in the one or more condition-specific cell variables for that feature-specific variant identifying the feature whose corresponding feature-specific variant-induced changes in the one or more condition-specific cell variables are most similar to the variant-induced changes in the one or more condition-specific cell variables.

The similarity between the feature-specific variant-induced changes in the one or more condition-specific cell variables and the variant-induced changes in the one or more condition-specific cell variables may be computed by summing the squares of their differences.

Although the invention has been described with reference to certain specific embodiments, various modifications thereof will be apparent to those skilled in the art without departing from the spirit and scope of the invention as outlined in the claims appended hereto.

We claim:

1. A computer-implemented method for computing a set of variant-induced changes in one or more condition-specific cell variables for one or more genetic variants, the method comprising:
   a. extracting a set of variant features from a DNA or RNA variant sequence, wherein the DNA or RNA variant sequence comprises the one or more genetic variants;
   b. processing the set of variant features using a cell variable predictor (CVP) to quantify one or more condition-specific variant cell variables, wherein the CVP comprises a deep neural network comprising at least two connected layers of processing units;
   c. extracting a set of reference features from a DNA or RNA reference sequence;
   d. processing the set of reference features using the CVP to quantify one or more condition-specific reference cell variables; and
   e. generating the set of variant-induced changes in the one or more condition-specific cell variables by processing the one or more condition-specific reference cell variables with the one or more condition-specific variant cell variables.

2. The method of claim 1, wherein:
   a. the DNA or RNA variant sequence or the DNA or RNA reference sequence is obtained by sequencing DNA or RNA from a sample of an individual;
   b. the DNA or RNA variant sequence is modified by applying a DNA or RNA editing system;
   c. the DNA or RNA variant sequence is modified by setting one or more nucleotides which are targeted by a therapy to fixed nucleotide values;

d. the DNA or RNA variant sequence is modified by setting one or more nucleotides which are targeted by a therapy to values that are different than existing nucleotide values; or e. the DNA or RNA variant sequence is modified by removing features that overlap, fully or partially, with nucleotides that are targeted by a therapy.

3. The method of claim 1, wherein extracting the set of variant features and the set of reference features comprises processing the DNA or RNA variant sequence or the DNA or RNA reference sequence to generate:

a. a binary matrix with 4 rows and a number of columns equal to a length of the DNA or RNA variant sequence or the DNA or RNA reference sequence, wherein each column contains a bit indicating the nucleotide value at the corresponding position in the DNA or RNA variant sequence or the DNA or RNA reference sequence;

b. a set of features computed using one or more layers of an autoencoder other than the input and output layers of the CVP; or c. a set of features that correspond to one or more of: RNA secondary structures, nucleosome positions, and retroviral repeat elements.

4. The method of claim 1, wherein the deep neural network comprises:

a. a convolutional neural network;

b. a recurrent neural network; or c. a long short-term memory recurrent neural network.

5. The method of claim 1, further comprising computing, using the CVP, probabilities for discrete levels of the condition-specific cell variables, wherein each of the set of variant-induced changes is computed by:

a. summing an absolute difference between the computed probabilities for the condition-specific reference cell variable and the condition-specific variant cell variable;

b. summing a Kullback-Leibler divergence between the computed probabilities of the condition-specific reference cell variable and the condition-specific variant cell variable for each condition; or c. computing an expected value of the condition-specific reference cell variable and the condition-specific variant cell variable, and subtracting the expected value of the condition-specific reference cell variable from the expected value of the condition-specific variant cell variable.

6. The method of claim 1, further comprising combining the set of variant-induced changes in the one or more condition-specific cell variables to compute a single numerical variant score for each of the one or more genetic variants, the single numerical variant score computed by:

a. outputting the score for a fixed condition;

b. summing the variant-induced changes across a plurality of conditions; or c. computing the maximum of the absolute variant-induced changes across a plurality of conditions.

7. The method of claim 6, further comprising applying thresholds that are fixed or selected using labeled data to the single numerical variant score for each of the one or more genetic variants to classify each of the one or more genetic variants (i) as one of deleterious or non-deleterious, (ii) as one of pathogenic, likely pathogenic, unknown significance, likely benign, or benign, or (iii) using another discrete set of labels.

8. The method of claim 1, further comprising computing for each of one or more pairs of the one or more genetic variants, a distance between the two genetic variants in each of the one or more pairs by summing the output of a nonlinear function applied to the difference between the change in the condition-specific cell variable for the first of the two genetic variants and the change in the condition-specific cell variable for the second of the two genetic variants.

9. The method of claim 8, further comprising determining deleteriousness labels or scores of each of the one or more genetic variants by computing a distance between each of the one or more genetic variants and one or more genetic variants of known deleteriousness and a) outputting a label or a score of the closest genetic variant of known deleteriousness; or b) computing a weighted average of the labels or scores of the genetic variants of known deleteriousness, wherein computing the weighted average comprises applying weights comprising nonlinear functions of the distances between each of the one or more genetic variants and the one or more genetic variants of known deleteriousness.

10. The method of claim 1, wherein the one or more genetic variants contain a) two or more distinct single nucleotide variants (SNVs); or b) a combination of substitutions, insertions, and deletions, wherein the combination is not a single nucleotide variant (SNV).

11. The method of claim 1, further comprising identifying an explanatory feature by:

a. generating a feature-specific variant feature vector by, for each of the set of variant features, copying a variant feature onto a corresponding reference feature;

b. processing the feature-specific variant feature vector using the CVP to generate a set of feature-specific variant-induced changes in the one or more condition-specific cell variables for the feature-specific variant feature vector; and c. identifying a feature whose corresponding feature-specific variant-induced changes are most similar to the set of variant-induced changes in the one or more condition-specific cell variables.

12. The method of claim 1, wherein the DNA or RNA variant sequence is obtained by or derived from (i) sequencing DNA or RNA from a sample of an individual or (ii) a reference human genome.

13. The method of claim 1, wherein the DNA or RNA reference sequence is obtained by or derived from (i) sequencing DNA or RNA from a sample of an individual or (ii) a reference human genome.

14. The method of claim 1, wherein the CVP comprises a single deep neural network.

15. The method of claim 1, further comprising generating a visualization of the set of variant-induced changes; and displaying the visualization of the set of variant-induced changes to a user on an output display.

16. The method of claim 6, further comprising generating a visualization of the single numerical variant score for each of the one or more genetic variants; and displaying the visualization of the single numerical variant score to a user on an output display.

17. The method of claim 7, further comprising generating a visualization of the classifications for the one or more genetic variants; and displaying the visualization of the classifications to a user on an output display.

18. The method of claim 9, further comprising generating a visualization of the deleteriousness labels or scores for the one or more genetic variants; and displaying the visualization of the deleteriousness labels or scores to a user on an output display.

19. The method of claim 1, further comprising generating a visualization of tissue-specific feature importance based on the set of variant-induced changes; and displaying the visualization of the tissue-specific feature importance to a user on an output display.

20. The method of claim 1, wherein the CVP is trained using a dataset of DNA or RNA sequences and corresponding measurements of cell variables.

21. The method of claim 1, further comprising determining an effect of an oligonucleotide therapy based on the generated set of variant-induced changes.

22. A computer-implemented method for computing a set of variant-induced changes in one or more condition-specific cell variables for one or more genetic variants, the method comprising:
 a. extracting a set of variant features from a DNA or RNA variant sequence, wherein the DNA or RNA variant sequence comprises the one or more genetic variants;
 b. processing the set of variant features using a cell variable predictor (CVP) to quantify one or more condition-specific variant cell variables, wherein the CVP comprises a deep neural network comprising at least two connected layers of processing units, wherein the deep neural network encodes a condition among a plurality of conditions in a layer of the at least two connected layers;
 c. extracting a set of reference features from a DNA or RNA reference sequence;
 d. processing the set of reference features using the CVP to quantify one or more condition-specific reference cell variables; and
 e. generating the set of variant-induced changes in the one or more condition-specific cell variables by processing the one or more condition-specific reference cell variables with the one or more condition-specific variant cell variables.

* * * * *